Figure 1A:
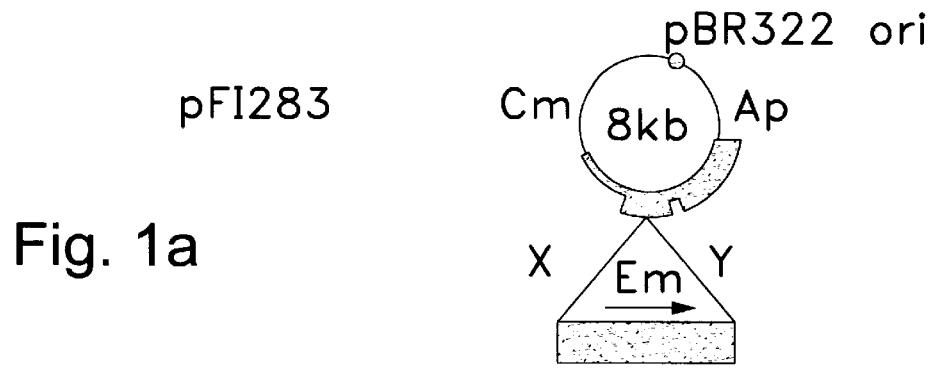

United States Patent [19]
Gasson et al.

[11] Patent Number: 6,100,056
[45] Date of Patent: *Aug. 8, 2000

[54] NISINS

[75] Inventors: Michael John Gasson, Dereham; Helen Mair Dodd, Norwich, both of United Kingdom

[73] Assignee: Biotechnology and Biological Sciences Research Council, Norwich, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/773,731

[22] PCT Filed: Apr. 1, 1993

[86] PCT No.: PCT/GB83/00676

§ 371 Date: Nov. 18, 1994

§ 102(e) Date: Nov. 18, 1994

[87] PCT Pub. No.: WO93/20213

PCT Pub. Date: Oct. 14, 1993

Related U.S. Application Data

[63] Continuation of application No. 08/313,123, Nov. 18, 1994.

[30] Foreign Application Priority Data

Apr. 2, 1992 [GB] United Kingdom .................. 9207267

[51] Int. Cl.[7] .............................. C12N 1/21; C12N 15/31; C12N 15/74
[52] U.S. Cl. .................... 435/69.1; 435/320.1; 435/471; 435/252.3
[58] Field of Search ............................... 435/69.1, 172.3, 435/320.1, 252.3, 253.4, 471

[56] References Cited

U.S. PATENT DOCUMENTS

| | | | |
|---|---|---|---|
| 4,990,452 | 2/1991 | Bryan et al. | 435/222 |
| 5,218,101 | 6/1993 | Hansen et al. | 536/23.7 |

FOREIGN PATENT DOCUMENTS 0 137 869 B1  4/1985  European Pat. Off. .
WO 92/18633  10/1992  European Pat. Off. .

OTHER PUBLICATIONS

Kuipers et al. "Expression of wild type and mutant nisin genes in *Lactococcus lactis*", pp. 250–259 in Jung and Sahl (ed.), Nisin and Novel Lantbiotics. ESCOM, Leiden, The Netherlands, 1991.

Chopin et al., "Insertion and amplification of foreign genes in the *Lactococcus lactis* subsp. *lactis* chromosome" Appl. Environ. Microbiol. 55: 1769–1774, Jul. 1989.

Lian et al., "Solution structures of nisin A and its two majordegradation products determined by n.m.r." Biochem J. 283: 413–420, 1992.

Gutterson et al., "Replacement and amplification of bacterial genes with sequences altered in vitro", Proc. Natl. Acad. Sci. USA 80: 4894–4898, Aug. 1983.

Kozak et al., "The effect of proflavin, ethidium bromide and an elevated temperature on the appearance of nisin–negative clones in nisin–producing strains of *Streptococcus lactis*", J. Gen. Microbiol. 83: 295–302, 1974.

Agriculture & Food Council et al., International Search Report, Int'l Appln. No. PCT/GB93/00676, Int'l Filing Date Apr. 1, 1993.

The Journal of Biological Chemistry, "Structure, Expression, and Evolution of a Gene Encoding the Precursor of Nisin, a Small Protein Antibiotic," George W. Buchman, Sharmila Banerjee and J. Norman Hansen (Nov. 5, 1988).

Applied and Environmental Microbiology, "A Lactococcal Expression System for Engineered Nisins," Helen M. Dodd, Nikki Horn, Zhang Hae and Michael J. Gasson (Nov. 1992).

*Primary Examiner*—Scott D. Priebe
*Attorney, Agent, or Firm*—Dickstein Shapiro Morin & Oshinsky LLP

[57] ABSTRACT

An organism which does not express its natural nisA gene product, but is capable of expressing genes for nisin modification, immunity and translocation out of the cell. The organism may be transformed with a coding sequence for a variant prenisin and appropriate regulatory sequences for expression thereof such that the organism is capable of secreting the corresponding variant nisin. A process for exclusively producing a variant nisin comprises fermenting this organism and obtaining the nisin so produced.

18 Claims, 15 Drawing Sheets

Fig. 2A pFI172 pFI354 pFI378

PCR amplification pFI411

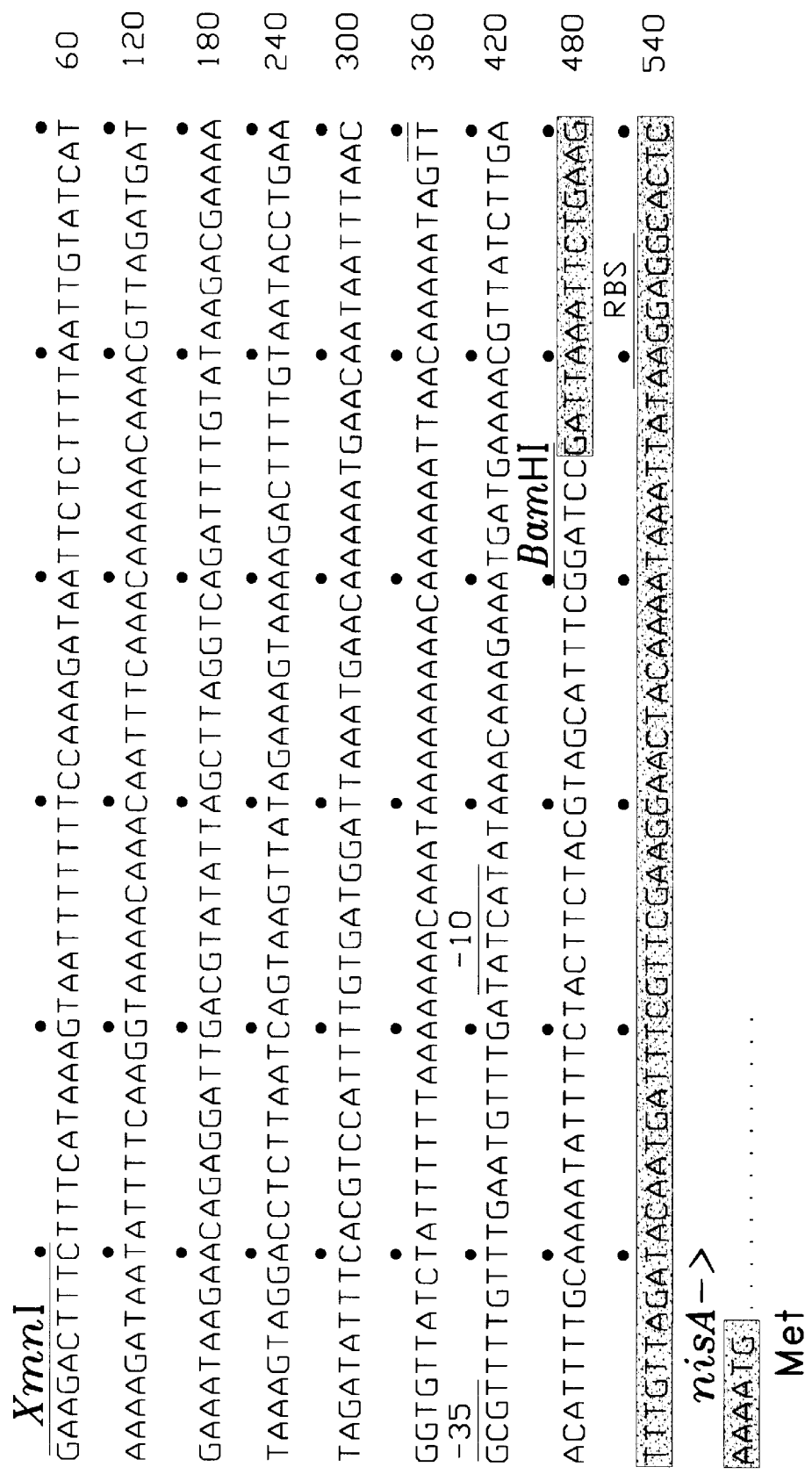

Fig. 9 nisin A/S5A
(Ala) ⇐

Ile¹—Dhb—Ala—Ile—Dha—Leu—Ala—Ala—Abu—Pro—Gly—Ala—Lys—Abu—Gly—Ala—Leu—Met—Gly—Ala—Asn²⁰—Met—Lys—Abu—Ala—Abu—Ala—His—Ala—Ser—Ile—His—Val—Dha—Lys³⁴ with thioether bridges labeled a, b, c, d, e and S–S connections forming rings nisin A/H27Q
(Gln) ⇐

IS905 sequence

```
                                                                                  •
GGTAGTGTAAATAAGTTGTGTAAACACAAAAAGGAATAAATCCGTTATAGTAGAGTTGC         60
        RBS
GAAACATTACTAGAAAGAGATTTATTCCTATGACTCAGTTTACCACAGAACTACTTAACT      120
                           M  T  Q  F  T  E  L  L  N
TCCTAGCCCAAAAGCAAGATATTGATGAATTTTTCCGTACTTCTCTTGAAACTGCTATGA      180
 F  L  A  Q  K  Q  D  I  D  E  F  F  R  T  S  L  E  T  A  M
ATGATCTGCTTCAAGCAGAGTTATCAGCCTTTTTAGGGTATGAACCTTACGATAAAGTAG     240
 N  D  L  L  Q  A  E  L  S  A  F  L  G  Y  E  P  Y  D  K  V
GCTATAATTCTGGGAATAGTCGTAACGGAAGCTATTCACGGCAATTTGAAACCAAATATG     300
 G  Y  N  S  G  N  S  R  N  G  S  Y  S  R  Q  F  E  T  K  Y
GGACTGTTCAGTTGAGCATTCCTAGAGATCGTAATGGAACTTAGTCCAGCTTTGCTTC        360
 G  T  V  Q  L  S  I  P  R  D  R  N  G  N  F  S  P  A  L  L
CCGCTTATGGACGTCGAGATGACCACTTGGAAGAGATGGTTATCAAACTCTATCAAACCG     420
 P  A  Y  G  R  R  D  D  H  L  E  E  M  V  I  K  L  Y  Q  T
GTGTAACGACTCGAGAAATTAGTGATATCATCGAGCGAATGTATGGTCATCACTATAGTC     480
 G  V  T  R  E  I  S  D  I  I  E  R  M  Y  G  H  H  Y  S
CTGCCACAATTTCTAATATCTCAAAAGCAACTCAGGAGAATGTCGCTACTTTTCATGAGC     520
 P  A  T  I  S  N  I  S  K  A  T  Q  E  N  V  A  T  F  H  E
GAAGCTTAGAAGCCAATTACTCTGTTTATTTCTTGACGAACCTATCTTCCATTAAGAC       600
 R  S  L  E  A  N  Y  S  V  L  F  L  D  G  T  Y  L  P  L  R
GTGGAACCGTTAGTAAAGAATGTATTCATATCGCACTTGGCATTACACCAGAAGGACAGA     660
 R  G  T  V  S  K  E  C  I  H  I  A  L  G  I  T  P  E  G  Q
```

Fig. 11A

```
AGGCTGTGTTCTTGGATATGAAATCGCCCCAAATCAAAAATAATGCTTCTCTTGGTCCACCCTGT    720
 K  A  V  L  G  Y  E  I  A  P  N  Q  N  N  A  S  W  S  T  L

TAGACAAGCTTCAAAAACCAAGGAATCCAACAGGTTTCTCTTGTAGTGACCGATGGCTTCA        780
 L  D  K  L  Q  N  Q  G  I  Q  Q  V  S  L  V  V  T  D  G  F

AGGGGCTTGAACAGATTATCAGGCTTACCCATTAGCTAAACAACAACGTTGCTTAA             820
 K  G  L  E  Q  I  I  S  Q  A  Y  P  L  A  K  Q  Q  R  C  L

TTCATATTAGTCGAAATCTAGTAGTAAAGTGAAACGAGCAGATAGAGCGGGTTATTCTGG         900
 I  H  I  S  R  N  L  A  S  K  V  K  R  A  D  R  A  V  I  L

AGCAATTTAAAACGATTTATCGTGCTGAAAATTTAGAAATGGCAGTGCAAGCTTTAGAGA         960
 E  Q  F  K  T  I  Y  R  A  E  N  L  E  M  A  V  Q  A  L  E

ACTTTATCGCCGAATGGAAACCAAAGTATAGGAAAGTCATGGAAAGTCTGGAGAATACGG        1020
 N  F  I  A  E  W  K  P  K  Y  R  K  V  M  E  S  L  E  N  T

ATAATCTTTTAACTTTTTATCAGTTCCCTACCAGATTTGGCACACATTTATTCGACAA          1080
 D  N  L  L  T  F  Y  Q  F  P  Y  Q  I  W  H  S  I  Y  S  T

ACCTCATTGAGTCTCTTAACAAACGTTACTTTGTTTGAAGATTATAATTTCAAGC             1140
 N  L  I  E  S  L  N  K  E  I  K  R  Q  T  K  K  V  L  F

CTAACGAGGAGGCTCTGGAACGTTACTTAGTTGTTACTTTGTTTGAAGATTATAATTTCAAGC     1200
 P  N  E  E  A  L  E  R  Y  L  V  T  L  F  E  D  Y  N  F  K

AAAGTCAACGCATCCATAAAGGGTTTGGCCAATGTGCTGACACTTGAAAGCTTATTTG          1260
 Q  S  Q  R  I  H  K  G  F  G  Q  C  A  D  T  L  E  S  L  F

ATTAATATTCTTCAACTCTACTTGAGTGTTTACACATAATTATTGACAGTATC    1313
 D  *
```

Fig. 11B

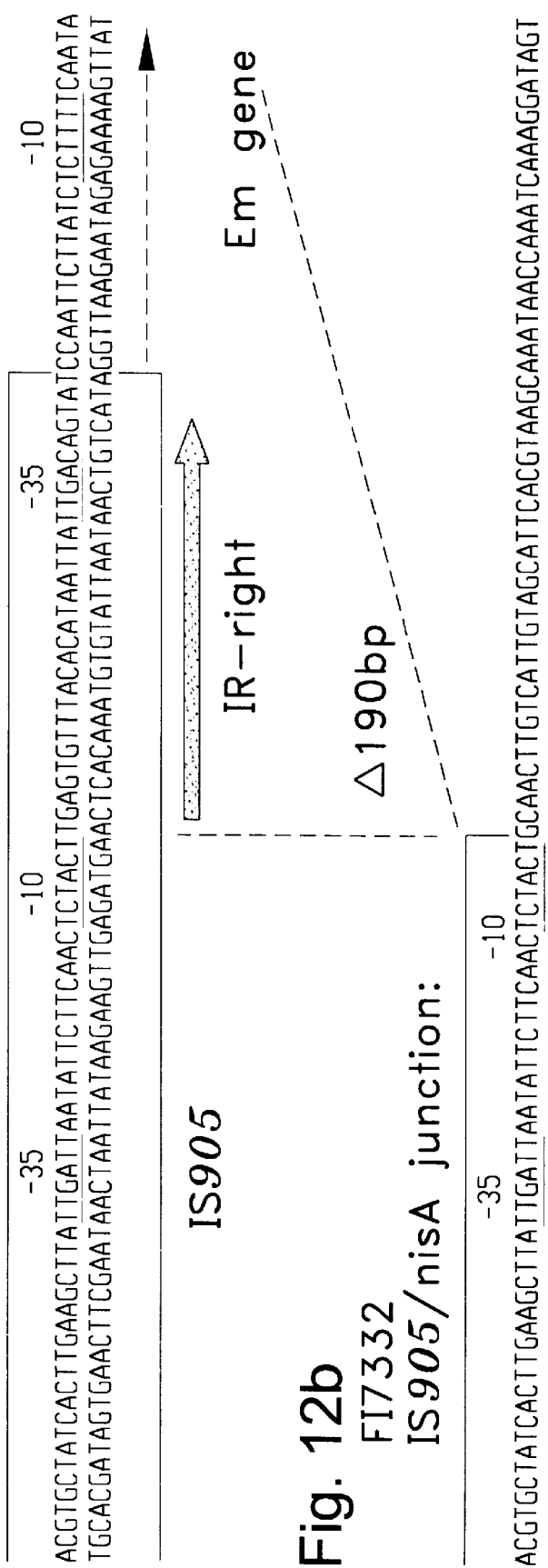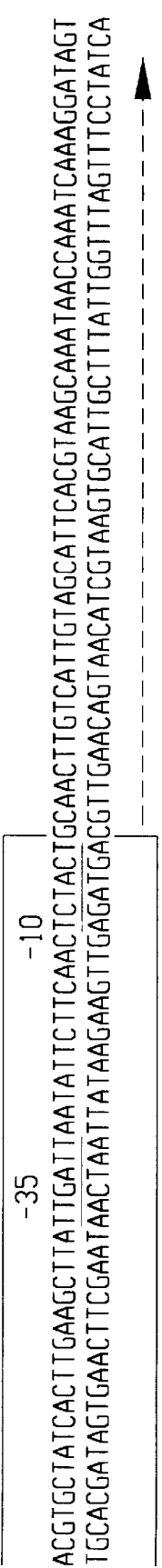

NISINS

This application is a continuation, of application Ser. No 08/313,123, filed Nov. 18, 1994, now abandoned, which is a 371 application of PCT/GB93/00676 filed Apr. 1, 1993.

This invention relates to the production of protein-engineered nisins.

Figure 2A:
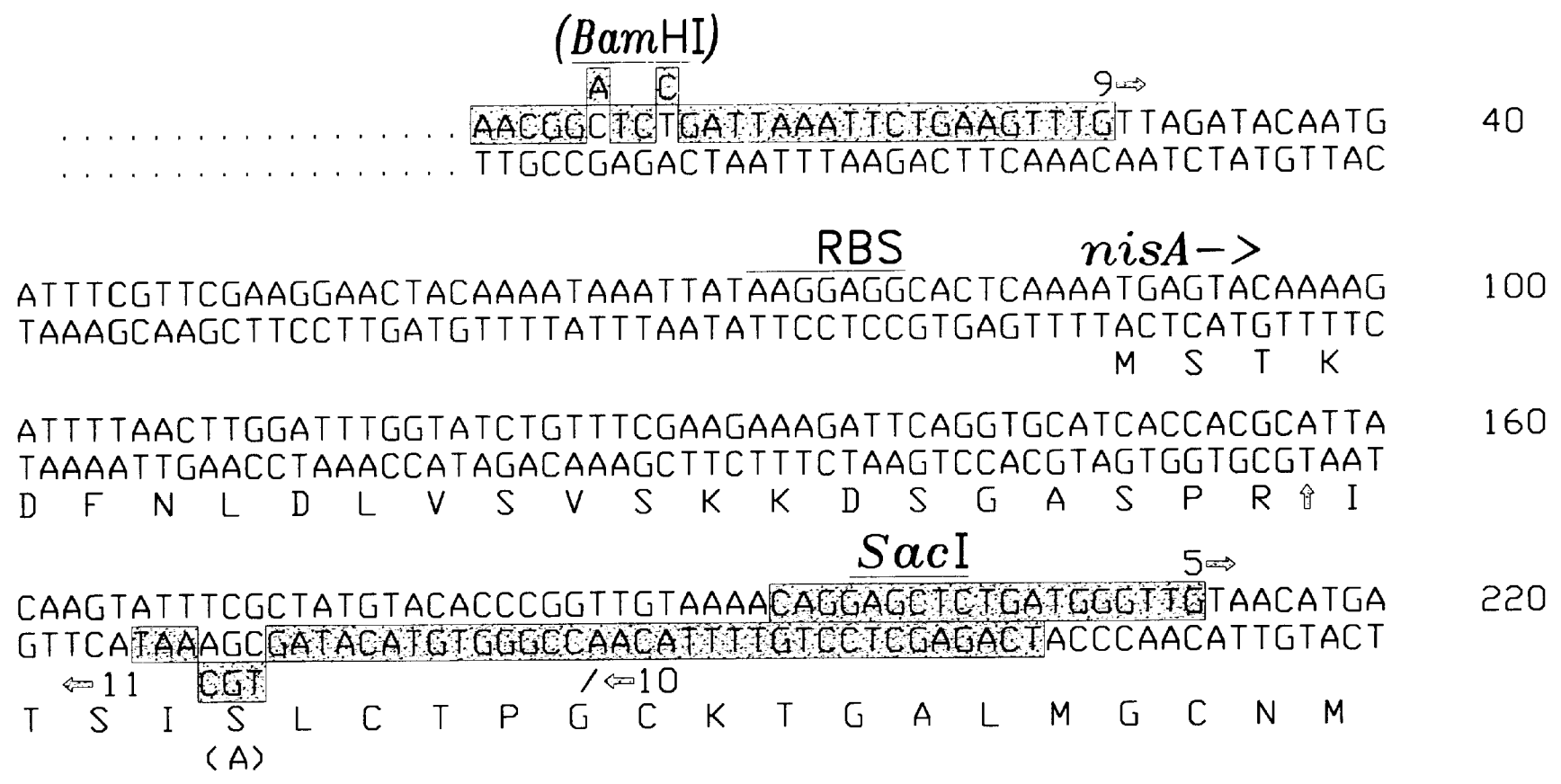
Figure 2B:
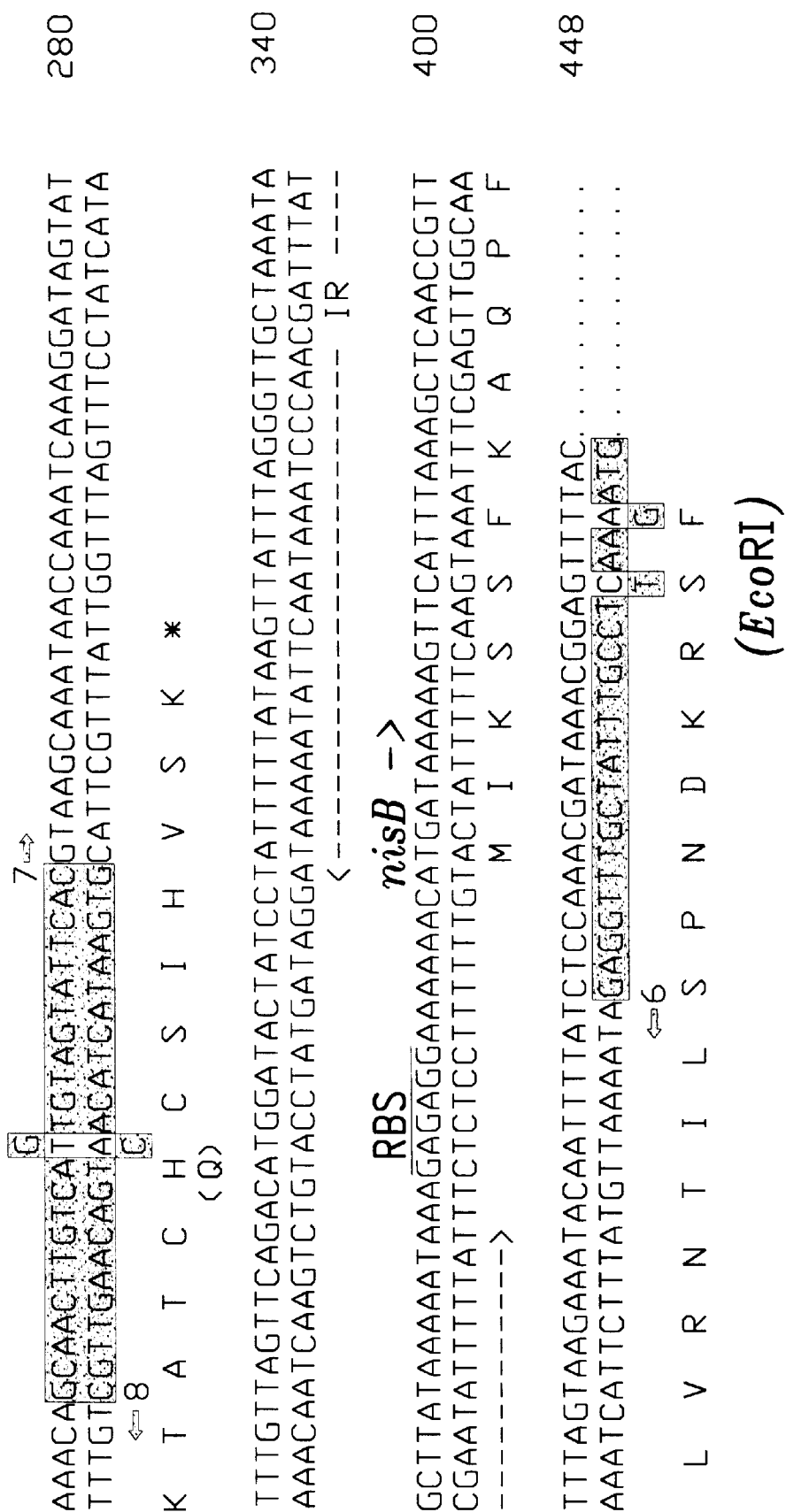
Figure 6A:
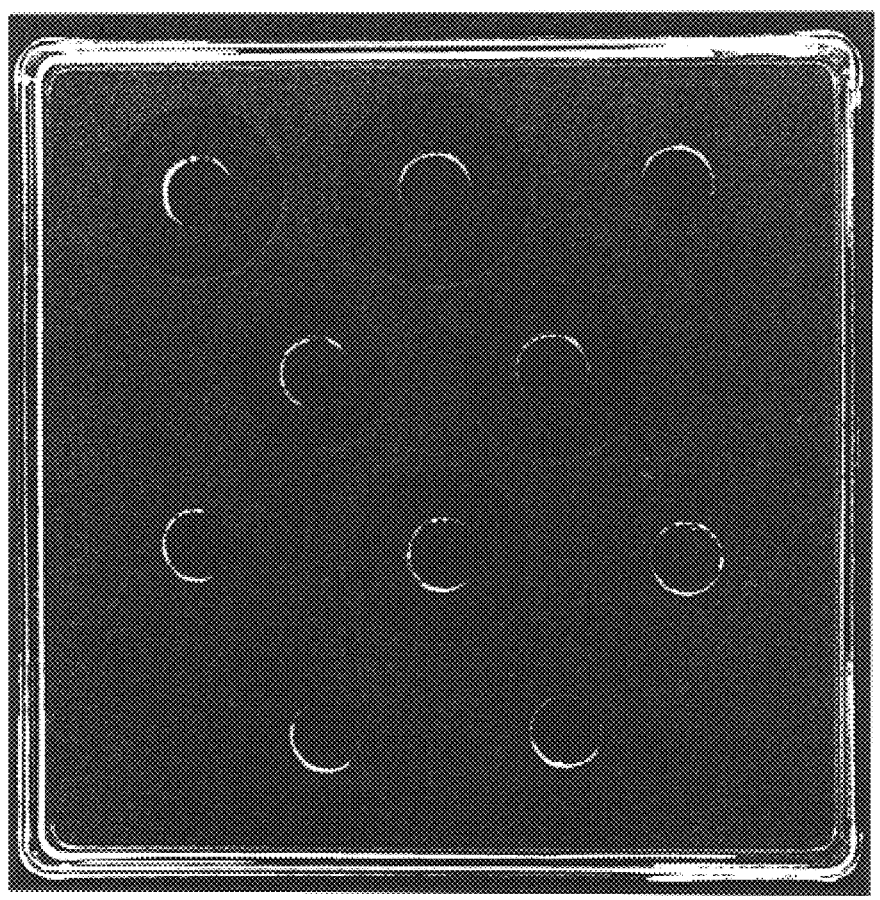
Figure 6B:
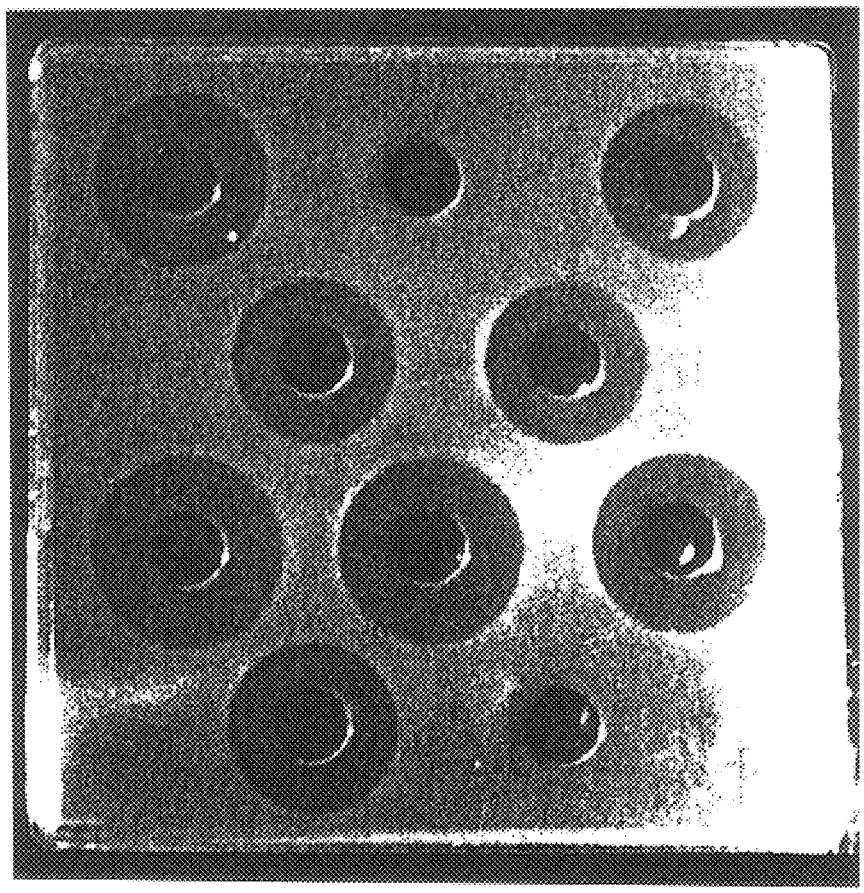

Reference to FIG. 2 herein, refers to FIGS. 2A and 2B collectively. Reference to FIG. 6 herein, refers to FIGS. 6A and 6B collectively. Reference to FIG. 11 herein, refers to FIGS. 11A and 11B collectively.

Nisin is a highly modified peptide antibiotic produced, for example, by certain strains of *Lactococcus lactis*. It is of great interest to the food industry because of its efficient antimicrobial activity against a wide range of gram-positive organisms including many spoilage bacteria and food pathogens, for example, Listeria, Clostridia and Bacillus species (12,25).

The chemical structure of nisin is well established (6,17, 34,45, FIG. 9) (SEQ ID NO:19). It is a member of the family of antibiotics termed lantibiotics. These unusual polycyclic peptides share the structural features of dehydro-residues and intrachain sulphide bridges forming lanthionine and β-methyllanthionine rings. The atypical residues are introduced by post-translational modification of amino acids serine, threonine and cysteine in the primary sequence of a precursor peptide (lantibiotics are the subject of a recent extensive review, 26). Biosynthesis of nisin thus involves genes for both the inactive precursor of nisin, known as prenisin, (nisA) and also the modifying enzymes responsible for nisin maturation. The mature nisin molecule is based on a sequence of 34 amino acids (SEQ ID NO:19). The protein encoded by nisA includes a 23 amino acid N terminal signal sequence which is cleaved off during secretion of nisin. The conversion of prenisin, encoded by nisA, into mature nisin involves cleavage of the leader and the modification of individual amino acids. The nisA gene has been cloned and characterised (1,27,11) and shown to have a chromosomal location (11,42). A number of additional, as yet uncharacterised, genes involved in the enzymatic modification of prenisin, translocation and immunity are encoded by nisin producing strains (42). These determinants, along with nisA, are thought to be clustered together as has been described recently for the lantibiotics subtilin (28) and epidermin (41). It has been known for some time that nisin determinants can be transferred by conjugation (14) and it has now been established that this ability is due to their carriage on a large conjugative transposon, Tn5301 (22,38).

Established protein engineering techniques can be used to introduce changes to the amino acid sequence of nisin. This involves modifying the coding region of the nisin structural gene, nisA, for example by site-directed or random mutagenesis. Expression of these changes is complicated by the fact that nisin is post-translationally modified.

Variant nisins may be constructed by the expression of variant nisA genes in a host strain which encodes the necessary maturation machinery, and thus can process the modified precursor peptide. The simplest approach is to transform a nisin producing strain with a recombinant plasmid encoding a variant nisA gene. In this background the host's maturation enzymes are available to process both the resident prenisin and its plasmid-encoded variant. A strategy of this type has been reported for a strain that carries the wild-type nisin transposon (29). However, the disadvantage of this system is that both the host's nisin and the engineered variant are synthesised together, making complex chemical separation procedures necessary prior to analysis of the properties of the novel peptide. Such a procedure would be particularly undesirable for industrial scale production of a variant nisin.

According to a first aspect of the present invention there is provided an organism which does not secrete its natural nisin, but is capable of expressing genes for nisin modification, immunity and translocation out of the cell.

By "an organism that does not secrete its natural nisin" we include an organism which does not naturally encode a nisin. Examples of organisms that do not naturally encode a nisin are *Bacillus subtilis* and *Escherichia coli*.

Preferably the organism is a lactococcal strain, most preferably *Lactococcus lactis*.

A second aspect of the present invention provides the organism described above transformed with a coding sequence for a variant prenisin and, if necessary, appropriate regulatory sequences for expression thereof, such that the organism is capable of secreting the corresponding variant nisin.

A third aspect of the present invention provides a process for producing a nisin comprising fermenting this organism and obtaining the nisin produced thereby.

By "nisin" it is meant a peptide antibiotic produced by some naturally occurring nisin producing strains of bacteria. The mature molecule is based on a sequence of amino acids encoded by a gene nisA.

By "variant nisin" it is meant a protein engineered variant of a natural nisin in which changes to the amino acid sequence of the nisin have been introduced as a result of site-directed or random mutagenesis of the nisA gene.

Site-directed mutations of the nisA gene may be made, for example, by the oligonucleotide-directed mutagenesis technique of Zoller & Smith (1983) *Meth. Enzymol.* 100, 468–500 and Zoller & Smith (1984) *DNA* 3, 479–480 which uses mismatched oligonucleotide primers to introduce the mutation.

It is convenient to use a method for improving the yield of mutants, for example, the dut-ung method described by Kunkel (1985) *Proc. Natl. Acad. Sci. USA* 82, 488–492. Alternatively, the polymerase chain reaction (PCR) may be used to generate mutants using mismatched oligonucleotides (Saiki et al (1988) *Science* 239, 487–491).

Random mutants of the nisA gene can be made chemically using, for example, sodium bisulphite or hydroxylamine as the mutagen. Alternatively, random mutations can be introduced into the nisA gene using enzymatic misincorporation using a DNA polymerase with relatively low fidelity, for example AMV reverse transcriptase or Taq DNA polymerase or by using mixtures of oligonucleotides, spiked during synthesis, to incorporate a small amount of each different bases at each position. These methods are well known in the art.

The derivation of an organism that expresses the maturation genes for nisin biosynthesis, but is deficient in its natural nisA gene product, thereby provides an effective means to produce variant nisins. The transformation of such a strain with a plasmid vector carrying an individual nisA gene containing a site-directed or random mutation generates a strain that produces exclusively a variant nisin.

As the gene for nisA is only one of a coordinately expressed group of genes that also provide the nisin modification, immunity and translocation functions, simple inactivation of the nisA gene does not yield a strain that is able to convert the product of a plasmid-encoded nisA gene into mature nisin.

A fourth aspect of the present invention provides a method of constructing an organism that does not secrete its natural nisin but is capable of expressing the other nisin genes. The method comprises selecting a nisin producing organism and selectively deleting the coding sequence for its natural nisA gene product or otherwise preventing the secretion of the nisin polypeptide, for example, by modifying an amino acid in the prenisin leader sequence, preferably amino acid 4.

A preferred method comprises insertionally inactivating the nisA gene and restoring the activity of the genes for nisin modification, immunity and translocation out of the cell. The restoration of activity may be achieved by selection in media containing nisin at inhibitory levels.

In another method the nisA gene is deleted or a mutation is introduced which prevents its translation and the expression of the associated nisin genes is maintained.

It will be appreciated by a person skilled in the art that an organism which does not naturally secrete nisin, and that does not naturally contain genes for nisin modification, immunity and translocation out of the cell may be converted into an organism useful in the practice of the present invention by transferring into it the said genes for nisin modification, immunity and translocation out of the cell. Thus, one embodiment of the invention provides a means of converting an organism which is not useful in the practice of the invention to one that is.

For example, it is possible to transfer the nisin modification, immunity and translocation genes from the *Lactococcus lactis* strain FI 7332 (as disclosed in the Example) to an organism that does not contain these genes, nor contains a nisA gene, for example *E. coli* or *B. subtilis* or a suitable lactococcal strain, by conjugation or transduction or by gene cloning technology. It is preferred if the organism is *B. subtilis* or a suitable lactococcal strain.

Furthermore, it is possible to transfer the nisin modification, immunity and translocation genes from a strain not able to produce a nisin (for example *Lactococcus lactis* strains FI 7300 and FI 7304 as disclosed in the Example) to an organism that does not contain these genes, introduce a nisA gene and then select for nisin production (that is, using similar methods to those disclosed in the Examples for the production of *Lactococcus lactis* FI 7300). Such a transfer of genes may also be by conjugation or transduction or gene cloning technology (including transformation in the case of the nisA gene). It is preferred if the organism is *B. subtilis* or a suitable lactococcal strain.

According to a fifth aspect of the present invention, the above-outlined method further comprises transforming the organism with a coding sequence for a variant prenisin and, if necessary, appropriate regulatory sequences for expression thereof. The organism is capable of post-translational modification of said prenisin and secretion of the corresponding variant nisin.

A sixth aspect of the present invention provides a nisin having a residue other than dehydroalanine corresponding to the residue in the first ring of natural nisin derived from the serine residue of unmodified prenisin. Said first ring of mature nisin is shown as ring a in FIG. 9 (SEQ ID NO:15).

A seventh aspect provides a nisin which does not have a dehydroalanine residue in the first ring. This variant nisin is preferably produced using the expression system of the present invention. A study of nisin breakdown during storage has revealed that activity is lost when the first ring of mature nisin becomes opened at amino acid 5 (5,34). This residue is dehydroalanine in mature nisin and it is derived by dehydration of a serine residue in prenisin. It is believed that the opening of the ring is due to the fact that the dehydroalanine is labile. A site-directed mutant of the nisA gene may be constructed in which the codon for serine at residue 5 of the natural prenisin is changed to one that encodes an amino acid other than serine. For example, codon for serine 5 may be changed to encode alanine, valine, threonine, leucine, isoleucine, glycine, histidine, arginine, lysine, aspartate, glutamate, asparagine, glutamine, proline, methionine, cysteine, phenylalanine, tyrosine or tryptophan. Alanine is preferred. The expression of the engineered nisA gene in a nisin producing organism in accordance with the present invention leads to the production of a variant mature nisin. In the case of the preferred mutation to an alanine codon, the variant mature nisin is named nisinA S5A. Investigations indicate that this variant nisin has greater stability than natural nisin A and is therefore an example of the exclusive production of an improved nisin.

The variant nisin not having dehydroalanine at position 5 may have other variations as well, although it is preferable to retain the dehydroalanine residue at position 33.

The amino acids replacing serine at position 5 may be modified post-translationally to form an amino acid not coded for directly, for example as disclosed herein for threonine residues.

Evidently, it is also possible to produce this variant nisin by expressing the engineered variant nisA gene on a plasmid vector that is transformed into a normal nisin producing organism. Mature variant nisin is produced as well as normal nisin.

It may also be possible to chemically synthesise the variant nisin peptides wherein Serine 5 is replaced by another amino acid residue.

Peptides, such as the variant nisins, may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethylacrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Using this chemical synthetic method it is possible to introduce non-natural amino acids into the synthetic nisin variant. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Alternatively, nisin variants, including those with an "unnatural" amino acid replacing serine at position 5, may be produced by in vitro cell-free translation.

Other variant nisins may also be exclusively produced using the expression system of the present invention. Retaining a dehydroalanine residue at positions 5 or 33 is preferred.

An active natural variant of nisin, known as nisin Z, has asparagine instead of histidine at amino acid 27 (15,37). A variant of nisin Z, for example, in which the amino acid corresponding to asparagine is changed to glutamine may be produced using a site-directed mutant of the nisA gene in the expression system. This variant nisin, named nisinA H27Q, has full biological activity.

Further aspects of the present invention provide the variant nisins produced using the expression system of the present invention, and the use of such nisins as antimicrobial agents.

The variant nisins of the present invention are particularly useful as antimicrobial agents in those conditions where the natural nisin is ring-opened and loses its antimicrobial properties. Such conditions include those of high pH present in many food situations and where the activity of normal nisin is limited. Preferred organisms to be killed include *Listeria monocytogenes* and Gram negative bacteria.

So that the invention may be more readily understood, preferred aspects will now be illustrated by way of example, and with reference to the accompanying drawings in which:

FIG. 1 illustrates the strategy for nisA gene replacement.

It shows a) a map of the gene replacement vector pFI283 and maps showing equivalent regions of chromosome encoding nisA and flanking sequences in strains b) FI5876, c) FI7181 and d) FI7300. The thin line represents plasmid DNA and the thick line represents lactococcal chromosomal DNA. The nisA and nisB genes are indicated by black boxed regions and DNA sequences containing the erythromycin resistance (Em$^r$) determinant are shown as shaded boxes. The direction of transcription of the genes is indicated by arrows above the maps. The small numbered arrows below the maps represent primers used in PCR analysis. A single recombination event between lactococcal sequences to the left of the Em$^r$ determinant on pFI283 and homologous sequences on FI5876 (X) results in Campbell integration of the plasmid with the organisation of sequences as shown in FI7181. Recombination between pFI283 sequences on both sides of the Em$^r$ determinant and homologous FI5876 sequences (X and Y) leads to gene replacement, as found with FI7300.

FIG. 2 shows the double stranded nucleotide sequence of the nisA gene and flanking regions (SEQ ID NO:1)

Coding regions preceded by ribosome binding sites (RBS) are indicated and the primary translation products (SEQ ID NO:2) are given below the sequence. The arrow between the arginine (R) at codon 154–156 and isoleucine (I) at codon 157–159 shows the point of cleavage of the N-terminal leader sequence of prenisin. Shaded regions represent the nucleotide sequences of synthetic oligomers employed as primers for PCR-mediated site-directed mutagenesis. The 3' end of the primers and the direction in which PCR proceeds is indicated by numbered arrows. The numbers refer to those primers as listed in methods. Specific mismatches included in the primers are represented by shaded nucleotides above or below the sequence. Primers 7 and 8 (SEQ ID NOS 14and 15, respectively) are designed to substitute a glutamine (Q) codon for a histidine (H) codon (coordinates 235–237) Primer 11 (SEQ ID NO:18) contains an alanine (A) codon in place of a serine (S) codon (coordinates 169–171). The primers containing restriction sites at their 5' ends define the termini of either PCR generated SacI/EcoRI restriction fragments (primers 5 and 6) (SEQ ID NOS 12 and 13, respectively) or BamHI/SacI restriction fragments (primers 9 and 10 or 9 and 11) (SEQ ID NOS 16 and 17, or SEQ ID NOS 16 and 18, respectively). The base changes mentioned above are incorporated in these fragments, which are then cloned into the expression vectors (see FIGS. 3 and 4) to reconstitute nisA genes containing the specific mutation.

FIG. 3 shows the construction of nisA expression vectors which use the natural nisin gene promoter.

The linear plasmid maps are of a) pFI172, b) pFI354, c) pFI378 and e) pFI411. Cloned Lactococcal DNA is represented by a thick line and vector sequences are indicated by a thin line. Genes within the cloned sequences are boxed and relevant restriction sites are given above the maps. d) illustrates the strategy employed for site-directed mutagenesis of the nisA gene to introduce the amino acid substitution His$^{27}$. Double stranded DNA sequence between the SacI and EcoRI sites shown in pFI378 (c) is represented by a double line. The sites at which primers anneal are indicated by arrows above and below the lines and the fragments which are amplified by PCR using combinations of these primers are represented by single thin lines. The mismatches incorporated in primers 7 and 8 (SEQ ID NOS 14 and 15, respectively) (see FIG. 2), and the mutation they generate in pFI411 (e), are indicated with an asterisk.

FIG. 4 shows the construction of nisA expression vectors for site-directed mutagenesis throughout the nisA gene using the lac promoter.

A PCR generated BamHI fragment, encoding the lacr gene and the divergently transcribed lacR and lacA promoters (18, ref), was digested with XmnI. The 0.45 kb restriction fragment (see FIG. 5) was subcloned into pTG262 to generate pFI451(a). Fragments N and C containing the N- and C-terminal regions of the nisA gene respectively, were constructed by PCR and cloned into pTG262 to generate pFI446(b). The nisA cassette contains the uninterrupted nisA gene preceded by 60 bp, including the RBS, and followed by an intergenic gap and the start of the nisB gene (SEQ ID NO:1as shown in FIG. 2). Vector pFI449 (c) contains the nisA cassette cloned into pFI451 as a BamHI/EcoRI restriction fragment. Vector pFI480 (d) contains the N-fragment of the nisA cassette cloned into pFI451 as a BamHI/SacI fragment. Vector pFI487 (e) contains the C-fragment of the nisA cassette cloned into pFI451 as a SacI/EcoRI fragment.

FIG. 5 shows the nucleotide sequence of the lactose operon promoter (SEQ ID NO:33)

The XmnI/BamHI fragment contains the lacA promoter and start of the nisA gene in the nisA cassette.

FIG. 6 shows plate diffusion bioassays.

Agar is seeded with the indicator strain *Lactobacillus helveticus* CH-1 and the wells contain samples of supernatants from various *Lactococcus lactis* subsp. lactis strains. Plate 1 shows that nisin A is produced by the FI7332 expression system as a result of complementation of the hosts nisA deficiency by plasmid encoded nisA genes. Furthermore, biological activity of the variant nisin A/H27Q is demonstrated. Wells contain supernatants from FI7330 (FI7332/pFI172 plasmid encoded nisA); FI5876 (nisin producing parent strain); MG1614 (non-nisin producing strain); FI7332/pFI411 (plasmid encoded nisA/H27Q); FI7332/pFI378 (plasmid encoded nisA); FI7332 plasmid free; and FI7332/pFI354 (plasmid vector for construction of variant nisA genes). Plate 2 demonstrates nisin activity by strains encoding nisA and the variant nisA/S5A gene under the control of the lacA promoter. Wells contain supernatants from FI5876 (nisin producing parent strain); FI7332 (plasmid free); FI7332/pFI378 (plasmid encoded nisA, natural promoter); FI7332/pFI449 (plasmid encoded nisA, lacA promoter); and FI7332/pFI493 (plasmid encoded nisA/S5A, lacA promoter). 100 μl of the following nisin standards (dissolved in 0.02M HCL) were loaded into some wells: 500 U/ml; 300 U/ml; 200 U/ml; 100 U/ml; and 0 U/ml.

FIG. 7 shows the construction of a host strain for the exclusive expression of mutant nisA genes.

Maps are of equivalent chromosomal regions of a) the nisin producing strain FI5876 and derivatives b) FI7300, c) FI7304 and d) FI7332. The nisA gene and the start of nisB gene are indicated by black boxes. The insertions in nisA are signified by a shaded box (Em$^r$, erythromycin resistance) and an open box (IS905). Primers employed for analysis of nisA insertional inactivation are shown as numbered arrows below the maps. Lines connecting primers represent the amplified fragment with sizes given in kilobases.

Figure 8:
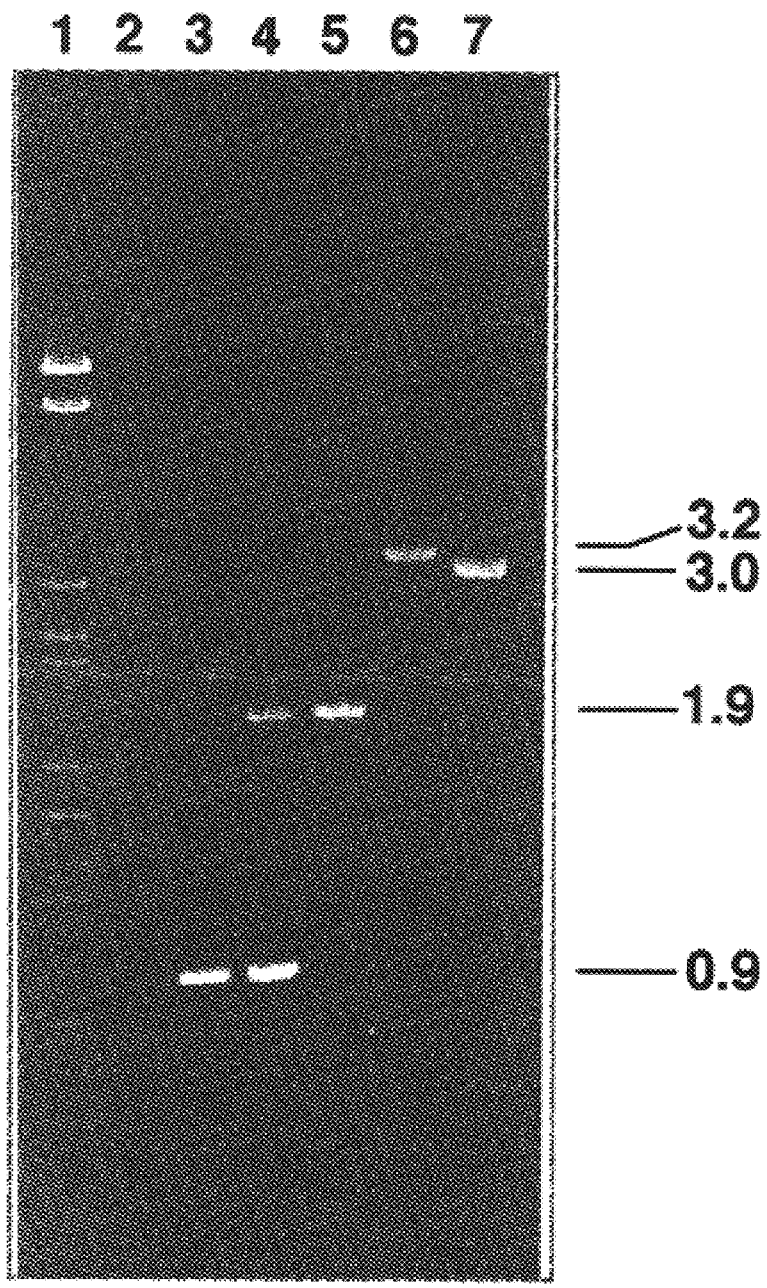

FIG. 8 shows PCR analysis of the constructed host strains.

PCR fragments generated with primers 1 and 2 (SEQ ID NOS 8 and 9, respectively) are separated by agarose gel electrophoresis. Template DNA from the non-nisin producing strain MG1614 is not amplified (track 2) whereas a band of 0.9 kb is generated from the nisin producing parent strain FI5876 (track 3). This band is also present when DNA from FI7181 is employed as template. However, Campbell integration of the gene replacement vector pFI283 in this strain (see FIG. 1c) results in the generation of a second band of 1.9 kb (track 4). In FI7330 (track 5) the nisA gene has been insertionally inactivated as a result of gene replacement (see FIG. 1d) and the 0.9 kb band is replaced with the 1.9 kb band containing the integrated Em$^r$ marker. This band is increased in size by a further 1.3 kb to 3.2 kb in FI7304 (track 6) as a result of insertion of IS905 in the Em$^r$ gene (see FIG. 7c). Strain FI7332 has undergone a 200 bp deletion at one end of IS905 (FIG. 7d) and a corresponding decrease in the equivalent PCR generated fragment results in a 3.0 kb band (track 7). Tracks 1 shows λDNA digested with BglI included as a size standard. The 1.2% agarose gel was run for 2.5 hours at 100 volts.

FIG. 9 shows the structure of nisin A (SEQ ID NO:19).

The modified residues are dehydroalanine (Dha), dehydrobutyrine (Dhb), aminobutyrate (Abu), lanthionine (Ala-S-Ala) and β-methyllanthionine (Abu-S-Ala). The predicted molecular alterations in Nisin A/H27Q and Nisin A/S5A are shown as amino-acid substitutions in ring e and ring a respectively.

Figure 10:
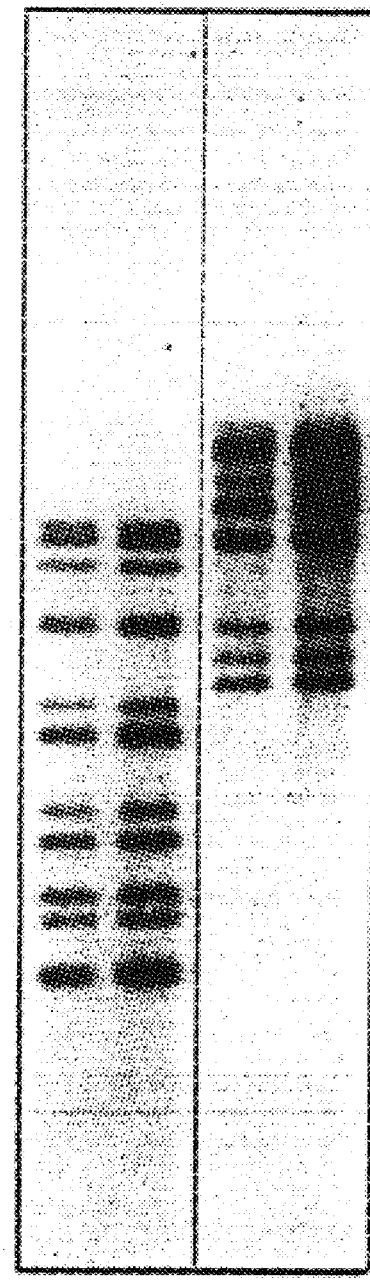

FIG. 10 illustrates the presence of multiple copies of DNA in the lactococcal genome.

Southern transfer hybridizations of restriction enzyme digested chromosomal DNA from MG1614 (tracks 1 & 3) and FI5876 (tracks 2 & 4). Restriction endonucleases HincII (tracks 1 & 2) and PvuII (tracks 3 & 4) were used. The filter was probed with a $^{32}$P-labelled gel-purified PCR fragment generated with primers 3 and 4 (SEQ ID NOS 10 and 11, respectively) using FI7304 DNA as template (see FIG. 7c). Multiple bands indicate that there are several regions that display homology to the probe which is characteristic of multicopy IS elements in the chromosome of these Lactococcal strains.

FIG. 11 shows the single stranded nucleotide sequence of insertion sequence IS905 (SEQ ID NO: 4) and its encoded polypeptide sequence (SEQ ID NO: 5).

The inverted repeats which define the termini of the element are underlined.

FIG. 12 shows the potential promoter active sequences at junctions generated by IS905 insertion in strains a) FI 7304 (SEQ ID NOS:6 and 20, respectively) and b) FI 7332 (SEQ ID NOS 7 and 21, respectively)

EXAMPLE

Microbiological techniques and strains used: Most *Lactococcus lactis* subsp. lactis strains, generated in the course of this work, were derived from the nisin producing strain *L. lactis* FI5876 (11,22). The construction of the derivative strains and their relevant properties are described in the results and in Table 1. The plasmid-free, non-nisin producing strain MG1614 (13) was included as a control. *L. lactis* strains were routinely grown at 30° C. in M17 media (43) supplemented with 0.5% (w/v) glucose (GM17). Selection for antibiotic resistance markers was as follows:- chloramphenicol resistance (Cm$^r$), 5 μg/ml; erythromycin resistance (Em$^r$) was induced at the subinhibitory level of 50 ng/ml followed by selection at 5 μg/ml.

TABLE 1

Characterisation of nisin producing strain FI5876 and derivatives.

| Strain | Em$^r$ | Nisin Production[a] | Nisin Immunity[b] (IU/ml) |
|---|---|---|---|
| MG1614 | − | − | <10 |
| FI5876 | − | + | 1–3 × 10$^3$ |
| FI7300 | + | − | 2–5 × 10$^2$ |
| FI7304 | − | − | 1–3 × 10$^3$ |
| FI7332 | − | − | 1–3 × 10$^3$ |

[a]nisin production was determined by the plate diffusion assay.
[b]levels at which strains were immune to nisin are given between two values. At the lower level growth was unaffected but inhibition of growth was evident at the upper level.

The *Escherichia coli* strain MC1022 (3) was the host strain used for construction of recombinant plasmids. Cultures were propagated at 37° C. in L broth (30). Selection for ampicillin resistance (Ap$^r$) was at 100 μg/ml and Cm$^r$ was at 15 μ/ml.

Determination of nisin production by *L. lactis* strains was based on the plate diffusion assay of Tramer and Fowler (44). *Lactobacillus helveticus* CH-1(Chr. Hansens Labs, Danmark A/S) was used as the nisin sensitive indicator strain. 0.5 ml of an overnight culture, grown in MRS media (9), was used to seed 50 ml MRS agar (pH 6.0) containing 1 ml Tween-20/Ringers solution (50:50). Wells were loaded with 100 μl of test sample and the plates incubated at 4° C. for a minimum of 3 hours (to allow diffusion) prior to overnight incubation at 42° C.

Nisin immunity was determined by streaking a loopful of stationary-phase cells on plates containing varying amounts of nisin. Nisin (Koch-Light), dissolved in 0.2 M HCl, was added to GM17 agar up to a maximum concentration of $5 \times 10^3$ U/ml at which growth of all strains was inhibited. *L. lactis* strains were considered to be immune to the highest level of nisin at which growth was evident throughout the streak.

Plasmid curing was achieved by growth in the presence of acriflavine (36).

Transformation: Recombinant plasmids were recovered by transformation of *E. coli* by the method of Cohen et al, 1972 (8) with the modification of Humphreys et al, 1979 (24). *L. lactis* strains were transformed by electroporation as described by Holo and Nes, 1989 (19) with the following modifications. Cells were grown in GM17 broth supplemented with 2% glycine and selection was made on GM17 plates containing antibiotic. Sucrose was omitted from the initial growth media and the selection plates. Electroporation was performed using the Gene Pulser apparatus (Bio-Rad).

Molecular techniques: Total genomic DNA from *L. lactis* strains was prepared according to the method of Lewington et al, 1987 (33). Plasmid DNA was isolated by the SDS alkaline lysis method. Purification of CCC DNA was by CsCl/EtBr gradient centrifugation (35). Restriction enzymes and other DNA modifying enzymes from various sources were used according to the suppliers recommendations. Conditions employed for PCR analysis were as described previously (22). The following primers were used in this study:

1. 5'-AAGAATCTCTCATGAGT; (SEQ ID NO:8)
2. 5'-CCATGTCTGAACTAACA; (SEQ ID NO:9)
3. 5'-GTGGAATACGGGTTTG; (SEQ ID NO:10)
4. 5'-TAAATAATTTATAGCTATTG; (SEQ ID NO:11)
5. 5'-CA<u>GAGCTC</u>TGATGGGTTG (SacI site underlined); (SEQ ID NO:12)
6. 5'-GTA<u>GAATTC</u>CGTTTATCGTTTGGAG (EcoRI site underlined); (SEQ ID NO:13)
7. 5'-GCAACTTGTCAGTGTAGTATTCAC; (SEQ ID NO:14)
8. 5'-GTGAATACTACACTGACAAGTTGC; (SEQ ID NO:15)
9. 5'-AAC<u>GGATCC</u>GATTAAATTCTGAAGTTTG (BamHI site underlined); (SEQ ID NO:16)
10. 5'-TCA<u>GAGCTC</u>CTGTTTTACAA (SacI site underlined); (SEQ ID NO:17)
11. 5'-TCA<u>GAGCTC</u>CTGTTTTACAACCGGGTGTACATAGTGCAAT (SacI site underlined); (SEQ ID NO:18)

All PCR amplified fragments generated were initially cloned into pUC18 (47) and the nucleotide sequence confirmed prior to vector construction. Nucleotide sequence determination of plasmid DNA was performed by the dideoxy chain termination method (40). Sequenase Version 2.0 was used according to the suppliers recommendations (United States Biochemical Corp.).

Site-directed mutagenesis was carried out using either PCR-mediated overlap extension or by incorporation of a specific mismatch into the particular primer used in the nisA fragment amplification.

Southern blot hybridisation and labelling of probes was performed according to published techniques (22).

Results

Insertional inactivation of the chromosomally located nisA gene: The gene replacement vector pFI283 was constructed to insertionally inactivate the chromosomally encoded nisA gene. It carries a cloned nisA gene which is disrupted by the insertion of an erythromycin resistance gene (FIG. 1a). Plasmid construction involved the following steps:

The nisA gene of FI5876 was cloned into the shuttle vector pTG262 to generate pFI172 which has been described previously (11,22). A 2 kb AccI/SalI fragment from this construct, containing nisA and the start of nisB, was subcloned into the pBR322 based vector, pMTL23P (4,46). A 1 kb fragment encoding the erythromycin resistance gene of the staphylococcal plasmid pE194 (20) was inserted into the unique SacI site within the cloned nisA gene. This insertion resulted in disruption of the nisA gene. The erythromycin resistance gene in this construct was transcribed in the same direction as the nisA gene and was flanked on either side by approximately 1 kb of lactococcal DNA sequences. A unique EcoRV site in the adjacent polylinker of the vector sequences was used to insert a 2 kb fragment carrying the chloramphenicol resistance gene originating from the staphylococcal plasmid pC194 (21). A map of the resulting recombinant plasmid, pFI283, is shown in FIG. 1a.

The nisin producing strain *L. lactis* FI5876 was transformed with pFI283 and erythromycin resistant transformants were obtained. The plasmid does not encode a replication origin functional in Lactococcus and hence the recovery of erythromycin resistance in these transformants required integration of this marker into the recipient chromosome.

Reciprocal recombination between homologous sequences on pFI283 (FIG. 1a) and the chromosome of FI5876 (FIG. 1b) could generate two types of transformants. A single cross-over event would result in the entire plasmid integrating in the chromosome (Campbell integration). A double cross-over event, one on either side of the erythromycin resistance gene in pFI283, would exchange the wild-type chromosomal nisA gene for the insertionally inactivated copy, with subsequent loss of chloramphenicol resistance encoded by the non-replicating plasmid (gene replacement). Both recombination mechanisms have been shown to operate in *Lactococcus lactis* (7,31,32). The two alternative types of recombination could be distinguished phenotypically in the transformants obtained by screening for chloramphenicol resistance. Transformants with only erythromycin resistance were recovered in which gene replacement had taken place (FIG. 1d). Strain FI7300 is typical of this construct.

Figure 1B:
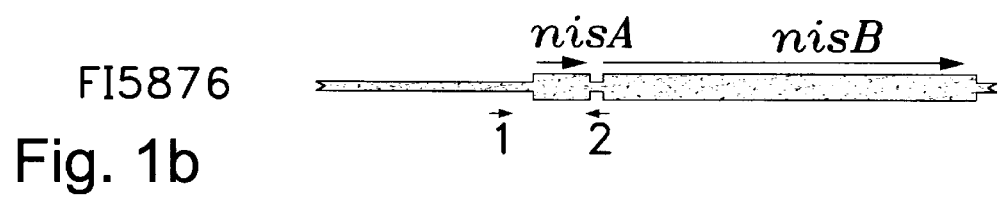
Figure 1C:
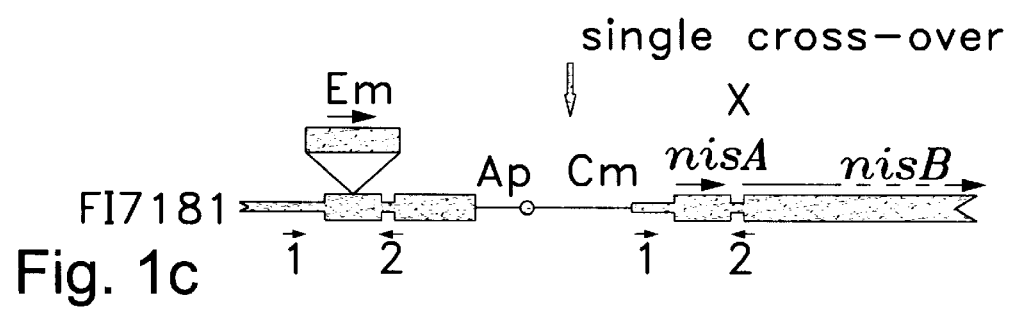
Figure 1D:
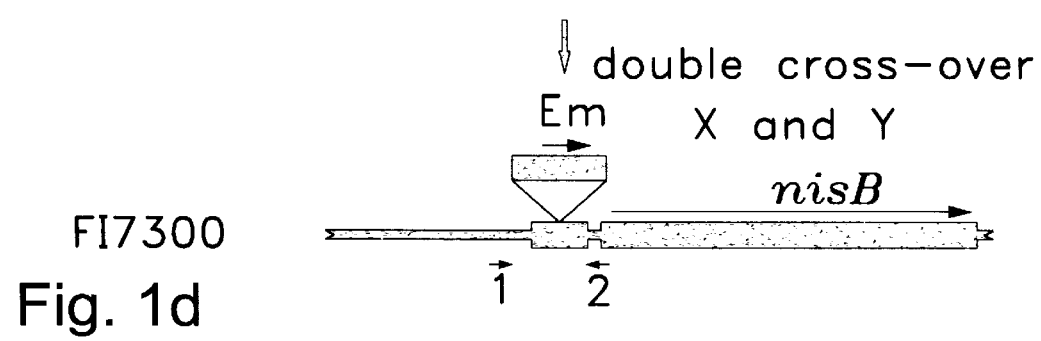

The chromosomal rearrangement was confirmed by PCR analysis using primers 1 and 2 (SEQ ID NOS 8 and 9, respectively) which specifically amplify a 0.9 kb fragment from FI5876 chromosomal sequences containing the nisA gene and flanking regions (FIG. 1b; FIG. 8, track 3). When DNA from FI7300, was used as template a 1.9 kb fragment was amplified by primers 1 and 2 (SEQ ID NOS 8 and 9, respectively) (FIG. 8, track 5). A 1 kb increase in size of this fragment would be expected if the erythromycin resistance gene was integrated in this part of the chromosome (FIG. 1d) and is consistent with the proposal that gene replacement had substituted the parental wild-type nisA gene with the insertionally inactivated copy.

Strain FI7300 having lost the parental nisA gene as a consequence of gene replacement no longer produced nisin. Furthermore the insertion in the nisA gene in this strain affected the nisin immunity level which was reduced to below 500 U/ml (Table 1).

In an attempt to recover nisin production in the nisA deficient host FI7300 the strain was transformed with pFI172, which encodes nisA, and six transformants were tested for nisin production. The bioassays gave negative results indicating that the chromosomal mutation in this host could not be complemented by provision of the nisA gene product in trans (Table 2).

Activation of genes for nisin immunity and modification: Reduction in nisin immunity due to the insertional inactivation of nisA in FI7300 may be caused by a polar effect on downstream genes. This may also result in reduced expression of genes required for modification thus preventing complementation of the nisA mutation in this host. In order to select derivatives of FI7300 in which the immunity and maturation genes were fully active mutation to wild-type levels of nisin immunity was selected by growth in media containing nisin at inhibitory levels. Colonies which grew on agar plates containing $10^3$ µg/ml nisin were picked and the cells grown on in media containing the same level of nisin. One such mutant, designated FI7304, expressed wild-type levels of nisin immunity, did not produce nisin and furthermore was no longer resistant to erythromycin (Table 1).

Figure 7A:
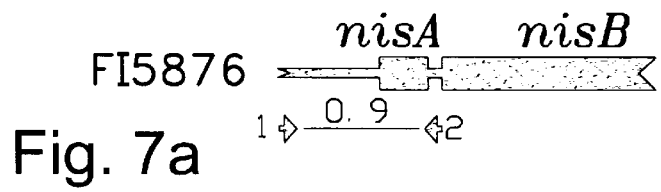
Figure 7B:
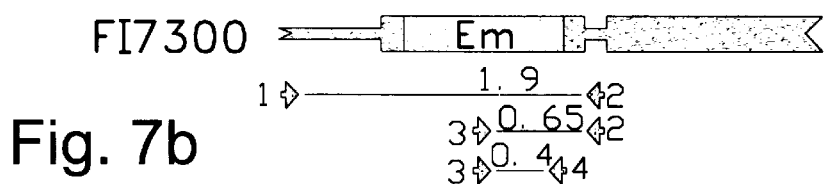
Figure 7C:
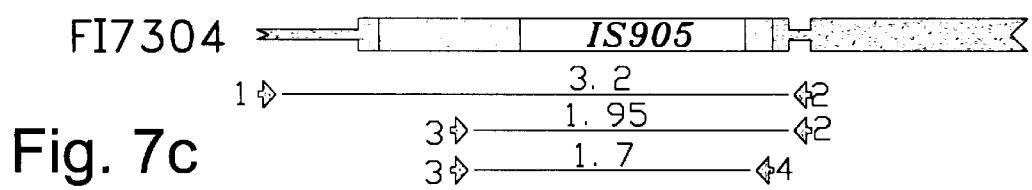

PCR analysis of FI7304 DNA, using primers 1 and 2 (SEQ ID NOS 8 and 9, respectively) resulted in amplification of a 3.2 kb fragment (FIG. 8, track 6), 1.3 kb larger than the equivalent FI7300 fragment generated by the same primers (FIG. 8, track 5). This suggested that loss of erythromycin resistance was not caused by a deletion in this region of the genome. The retention of the erythromycin resistance gene sequences was confirmed by PCR using primers 3 and 4 (SEQ ID NOS 10 and 11, respectively), which are specific for a region at the 3' end of that gene and amplify a 0.4 kb fragment (FIG. 7b). As these primers generated an FI7304 fragment 1.7 kb in size it was concluded that an additional 1.3 kb of DNA was inserted in this region of the erythromycin resistance gene (FIG. 7c). This insert results in loss of erythromycin resistance with concurrent recovery of nisin immunity (see below). A comparison of fragments from FI7300 and FI7304 generated by amplification between primers 3 and 2 (SEQ ID NOS 10 and 9, respectively) and primers 3 and 4 (SEQ ID NOS 10 and 11, respectively) was consistent with this interpretation (FIG. 7b and c).

The extra DNA sequences gained by FI7304 were amplified with primers 3 and 4 (SEQ ID NOS 10 and 11, respectively) (FIG. 7c) and this PCR fragment was used to probe a southern blot of restriction enzyme digested genomic DNA from the parent strain, FI5876. A number of fragments hybridised to the probe (FIG. 10) indicating that the additional DNA in FI7304 is present in multiple copies in the genome of this strain. Further investigation has revealed that these repeated sequences represent a new lactococcal insertion sequence designated IS905, the sequence of which is presented in FIG. 11. As has been demonstrated for other IS elements (2,39,48), transcriptional read-through from a potential promoter within IS905 may lead to turn-on of downstream genes. The IS element IS905 was found to have significant homology with IS256, which is known to express an adjacent antibiotic resistance gene from an internal promoter (2,39). Such promoter activity could account for the observed increase in nisin immunity exhibited by FI7304 which is equivalent to that of the parent strain, FI5876 (Table 1) and it may also have restored the expression of genes required for processing of prenisin to a level sufficient to facilitate nisA complementation. The DNA sequences of the junction of IS905 and the Em gene in FI 7304 and of IS905 and the nisA gene in FI 7332 are shown in FIG. 12.

Expression and maturation of plasmid encoded nisA: FI7304 was transformed with the nisA encoding plasmid, pFI172. Transformants were obtained at low frequency and the majority did not produce nisin in bioassays. One transformant, designated FI7330, was found to yield nisin at a level approximately 50% that of the parent strain FI5876 (FIG. 6). It was presumed that FI7330 had undergone a spontaneous mutation, either within the plasmid or the chromosome sequences, which resulted in nisin production. Isolation of plasmid DNA from FI7330 yielded a molecule indistinguishable from pFI172 on the basis of restriction enzyme analysis. Curing FI7330 of plasmid DNA, to generate the plasmid free strain FI7332, resulted in loss of nisin production (FIG. 6). However, when plasmid pFI172 was introduced back into the latter strain high transformation frequencies were obtained (FIG. 12) and all transformants produced nisin in bioassays.

Figure 7D:
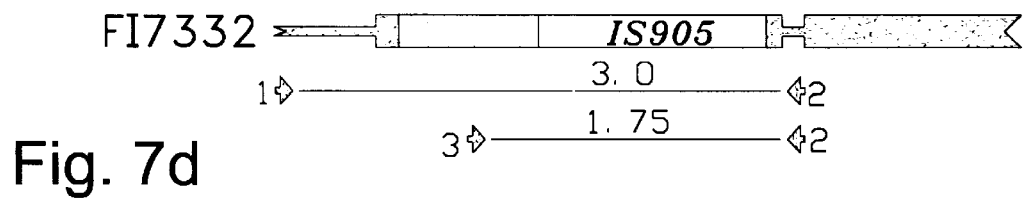

When DNA from the plasmid free strain, FI7332, was analysed by PCR using primers 1 and 2 (SEQ ID NOS 8 and 9 respectively) a small size reduction (200 bp) was observed in the amplified fragment. The deletion was in the vicinity of the IS905 insertion in FI7304 (FIG. 8, cf tracks 5 and 6). Primers 3 and 4 (SEQ ID NOS 10 and 11 respectively) (derived from the erythromycin resistance gene sequences, (FIG. 7b) did not generate a fragment with this template (FIG. 7d) indicating that the deleted sequences in FI7332 included a region at the 3' end of the erythromycin resistance gene into which IS905 had inserted. The deletion does not extend beyond the nisA gene as primer 2 (SEQ ID NO:9) (specific for sequences at the end of nisA), together with either primers 1 or 3 (SEQ ID NOS 8 and 10 respectively), resulted in fragment amplification (FIG. 7d). The small chromosomal rearrangement in FI7332 has not affected nisin immunity which is conferred at a level indistinguishable from that of the parent strain (Table 1).

Expression of variant nisA genes: To produce engineered nisin molecules PCR-mediated site-directed mutagenesis was carried out on the nucleotide sequence of the nisA gene. The expression vectors pFI354 (FIG. 3b) and pFI451 (FIG. 4a) were designed for the expression of site-directed mutants of the nisA gene.

Figure 3A:
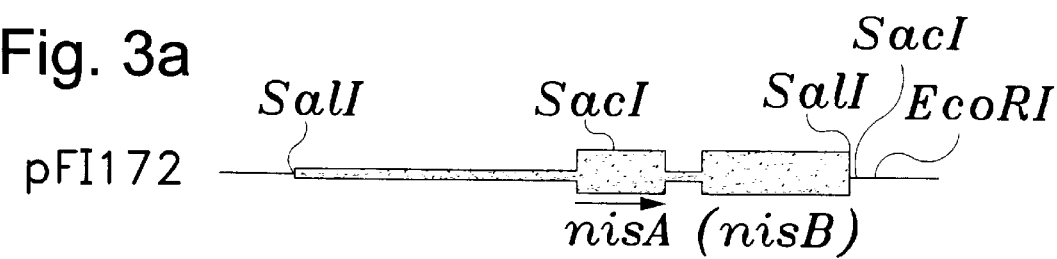
Figure 3B:
Figure 3C:
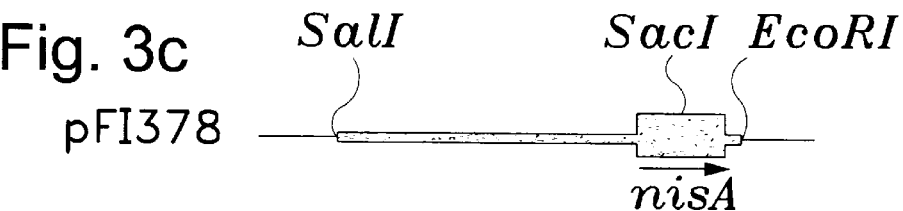
Figure 3D:
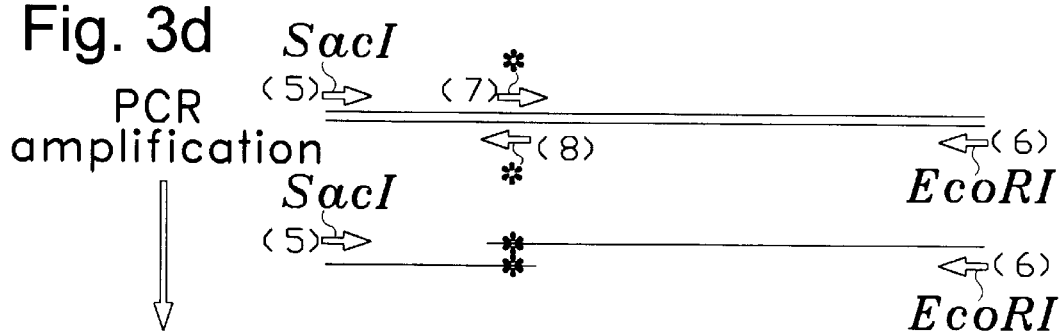

Plasmid pFI354 was constructed by deletion of a 1.25 kb SacI fragment from pFI172. It thus encodes only the N-terminal part of nisA (FIG. 3b). Using PCR the C-terminal part of the nisA gene was amplified as a 254 bp SacI/EcoRI fragment. By cloning this fragment into pFI354 an intact nisA gene could be reconstituted as in pFI378 (FIG. 3c). Adaptation of this procedure enabled predetermined substitutions to be introduced into the C-terminal region of the nisA gene (using site-directed mutagenesis, see below). These pFI354 derivatives utilize the natural promoter of the nisin operon which lies between the SalI site defining one end of the cloned chromosomal fragment and the start of the nisA gene (FIG. 3). In this system the incorporation of site-directed mutations is limited to sequences in the nisA coding region downstream of the SacI site (FIG. 2) (SEQ ID NOS 1 and 2, respectively).

Initially the nisA codon selected for alteration was Histidine[27] which lies within ring 5 of the mature nisin A molecule (FIG. 9) (SEQ ID NO:19). A naturally occurring variant of nisin A, termed nisin Z, has been identified which contains an Asparagine residue in place of Histidine[27] (15,23,37). The engineered incorporation of a similarly charged Glutamine in place of Asparagine at residue 27 would thus represent a conservative substitution in the nisin Z amino acid sequence. The mutation involved a single base pair change in the PCR generated SacI/EcoRI fragment carrying the C-terminal end of nisA (FIG. 2) (SEQ ID NOS 1 and 2, respectively). The reconstituted gene, containing a Glutamine codon (CAG) in place of a Histidine codon (CAT.

Figure 3E:
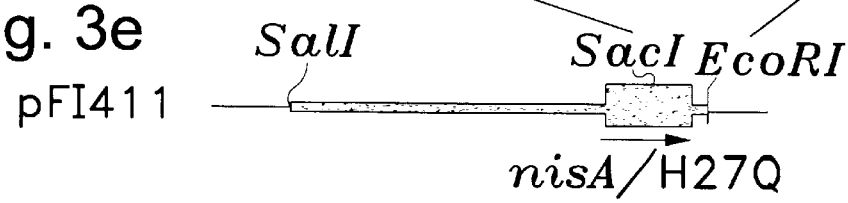

FIG. 2) (SEQ ID NOS 1 and 2, respectively) was designated nisA/H27Q in accordance with agreed nomenclature (10). Site-directed mutagenesis was carried out using PCR-mediated overlap extension (FIG. 3d) as follows:

Terminal primers 5 and 6 (SEQ ID NOS 12 and 13, respectively) contain a SacI site and an EcoRI site respectively and define the ends of a 254bp fragment encoding the C-terminal 20 amino acids of prenisin (FIG. 2) (SEQ ID NOS 1 and 2, respectively). A pair of overlapping complementary primers (7 and 8) (SEQ ID NOS 14 and 15, respectively) were designed from sequences within the C-terminal region of nisA which included a single base change from the original nisA sequence (FIG. 2) (SEQ ID NOS 1 and 2, respectively). These were used in PCR amplifications in conjunction with one of the terminal primers (FIG. 3d) to create two partially complementary fragments with the specific mutation located in the overlapping region. The fragments were annealed to provide a template for subsequent PCR involving the same terminal primers that determined the two ends of the SacI/EcoRI fragment (primers 5 and 6, (SEQ ID NOS 12 and 13, respectively) FIG. 3d). The final PCR generated fragment containing the specific mutation was purified by isolation from an agarose gel using DEAE-NA 45 membrane (Schleicher and Schuell). Modification of ragged ends was carried out using T4 DNA polymerase and polynucleotide kinase. The blunt ended fragment was cloned into the SmaI site of pUC18 and the nucleotide sequence of the manipulated region determined to confirm that the selected mutation was present. A SacI/EcoRI fragment from the pUC18 derivatives was then subcloned into pFI354 to recover an uninterrupted nisA reading frame containing the predetermined mutation. This plasmid was designated pFI411 (FIG. 3e).

Vectors pFI480 and pFI487 were constructed in which expression of the nisA gene was under the control of the lacA promoter (FIG. 4). In order to introduce changes throughout the entire nisin molecule a nisA gene cassette was constructed. Using PCR with primers 9 and 10 (SEQ ID NOS 16 and 17, respectively) (FIG. 2) the N-terminal part of the nisA gene was amplified as a 200 bp BamHI/SacI fragment. This fragment was cloned into plasmid pFI354 upstream of the 254bp SacI/EcoRI fragment encoding the C-terminal part of nisA. The latter was generated by PCR using primers 5 and 6 (SEQ ID NOS 12 and 13, respectively) as described above. In this way an intact coding region for the whole nisA gene, lying within a 448 bp BamHI/EcoRI fragment, was reconstituted from two PCR generated fragments which encoded the N and C parts of the nisin molecule. The resultant plasmid was designated pFI446 (FIG. 4). The nisA cassette includes the upstream nisA ribosome binding site and the start of the nisB gene (FIG. 2) (SEQ ID NO:1).

As the natural promoter of nisA is not part of this cassette, the inducible lacA promoter of the lactococcal lactose operon (18, FIG. 5) (SEQ ID NO:3) was employed for expression of nisA and subsequent variant nisA genes. Vector construction involved cloning a XmnI/BamHI fragment containing the lacA promoter, but excluding the lacA ribosome binding site, into pTG262 to generate pFI451 (FIG. 4). Into the adjacent polylinker was cloned the entire nisA cassette on a BamHI/EcoRI fragment to generate pFI449. The individual components of the nisA gene described above ie the 200 bp BamHI/SacI N-fragment and the 254 bp SacI/EcoRI C-fragment, were also separately cloned into pFI451 to generate pFI480 and pFI487, respectively (FIG. 4). To recover an intact nisA gene in these plasmids, insertion of the missing N or C fragment is required. These fragments can be generated by PCR and using appropriate primers, site-specific substitutions can be incorporated into the reconstituted gene (see below).

Using this expression system the amino acid initially selected for alteration was Serine[5]. In mature nisin A, Serine[5] is modified to a dehydroalanine residue in ring A (FIG. 9) (SEQ ID NO:19). The aim was to replace this with an Alanine residue by incorporating the required mutation in the N-terminal fragment of the nisA cassette using PCR methodology. Primer 11 (SEQ ID NO:18), which contains an alanine codon (TGC) in place of the Serine[5] codon (CGA), was used together with primer 9 (SEQ ID NO:16) (FIG. 2) to generate an amino-terminal fragment carrying this specific mutation. Primer 11 (SEQ ID NO:18) comprises primer 10 (SEQ ID NO:17) sequences with an additional 20 nucleotides including an alanine codon in place of the wild type serine codon (FIG. 2). Thus, PCR amplification of nisA using primers 9 and 11 (SEQ ID NOS 16 and 18, respectively) generated an N-terminal fragment carrying the specific substitution and subsequent insertion of this BamHI/SacI fragment into pFI487 resulted in a variant nisA gene containing the desired site-specific mutation. The plasmid encoding this variant nisA gene (nisA/S5A) was designated pFI493.

Figure 4A:
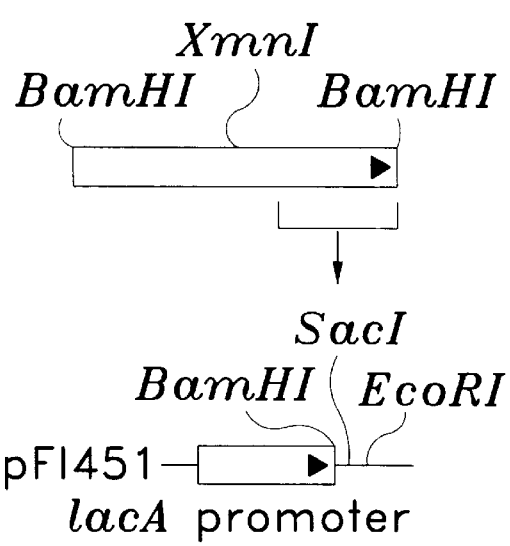
Figure 4B:
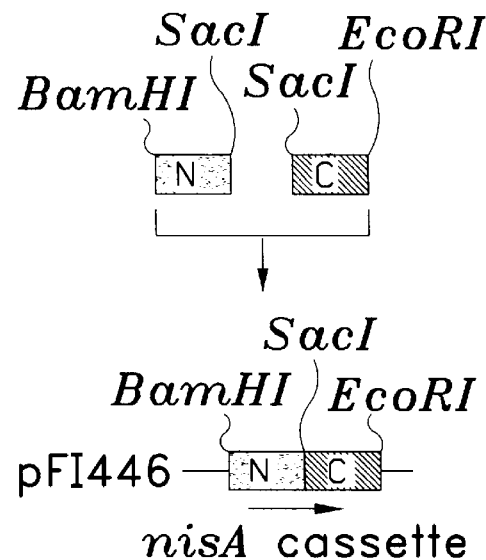
Figure 4C:
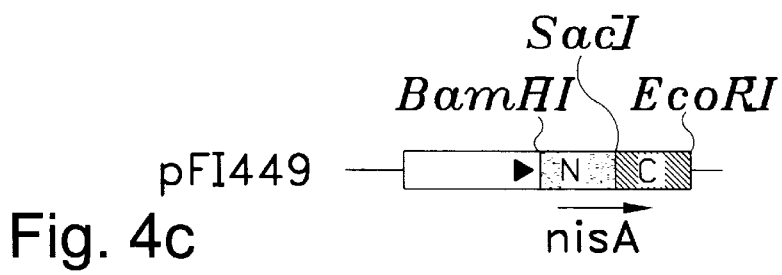
Figure 4D:
Figure 4E:

The Nis⁻ strain FI7332 was transformed with plasmids which encode the nisA gene under the control of either its own promoter (pFI378, FIG. 3c) or the lacA promoter (pFI449, FIG. 4c). When transformants were tested in plate diffusion assays biological activity was detected at a level approximately 50% that of the wild-type parent strain FI5876 (FIG. 6., Table 2). The difference in the expression vector promoters did not appear to significantly affect the level of biological activity (FIG. 6, Table 2).

Transformants of FI7332 containing derivatives of the expression vectors encoding variant nisA genes were also tested for biological activity. Strains encoding nisA/H27Q and nisA/S5A exhibited nisin activity at levels lower than that of FI5876, but comparable to those levels achieved in the expression systems involving nisA complementation (ie FI7332/pFI378 and FI7332/pFI451; Table 2, FIG. 6).

TABLE 2

Expression of nisA and variant nisA genes in different host strains.

| Strain | Plasmid | Nisin gene | Nisin activity[a] |
|---|---|---|---|
| FI5876 | — | nisA | ++ |
| MG1614 | — | — | − |
| " | pFI172 | nisA | − |
| FI7300 | — | — | − |
| " | pFI172 | nisA | − |
| FI7304 | — | — | − |
| FI7330[b] | pFI172 | nisA | + |
| FI7332 | — | — | − |
| " | pFI172 | nisA | + |
| " | pFI354 | — | − |
| " | pFI378 | nisA | + |
| " | pFI411 | nisA/H27G | + |
| " | pFI499[c] | nisA | + |
| " | pFI493[c] | nisA/S5A | + |

[a] nisin activity was measured by the plate diffusion assay. Zones of inhibition of growth were: ++, 24 mm and +, 18–21 mm (including the 8 mm bore of the well).
[b] FI7330 was generated by transforming FI7304 with pFI172 followed by a chromosomal deletion (see text). As the host strain is no longer FI7304 a new strain number was allocated.
[c] plasmids are derivatives of pFI451 (FIG. 4a) in which the nisA cassette is preceded by the lacA promoter. All other plasmids utilise the natural nisA promoter.

REFERENCES

1. Buchman, W. B. et al (1988) *J. Biol. Chem.* 263, 16260–16266.
2. Byrne, M. E. et al (1989) *Gene* 81, 361–367.
3. Casadaban, M. J. & Cohen, S. N. (1980) *J. Mol. Biol.* 138, 179–207.
4. Chambers, S. P. et al (1988) *Gene* 68, 139–149.

5. Chan, W. C. et al (1989) *FEBS Letts.* 252, 29–36.
6. Chan, W. C. et al (1989) *J. Chem. Soc. Perkin. Trans.* 1, 2359–2367.
7. Chopin, M. C. et al (1989) *Appl. Environ. Microbiol.* 55, 1769–1774.
8. Cohen, S. N. et al (1972) *Proc. Natl. Acad. Sci., USA.* 69, 2110–2114.
9. De Man, J. C. et al (1960) *J. Bacteriol.* 23, 130–135.
10. De Vos, W. M. et al (1991) In "*Nisin and novel lantibiotics*" (eds. G. Jung & H-S. Sahl) pp. 457–463. ESCOM, Leiden.
11. Dodd, H. M. et al (1990) *J. Gen. Microbiol.* 136, 555–566.
12. Fowler, G. G. & Gasson, M. J. (1990) In *Food Preservatives* (eds. N. J. Russel & G. W. Goulds) pp. 135–152. Blackie and Sons, Glasgow.
13. Gasson, M. J. (1983) *J. Bacteriol.* 154, 1–9.
14. Gasson, M. J. (1984) *FEMS Microbiol. Letts* 21, 7–10.
15. Graeffe, T. et al (1991) In "*Nisin and novel lantibiotics*" (eds. G. Jung & H-S. Sahl) pp. 260–268. ESCOM, Leiden.
16. Graves, M. C. & Rabinowitz, J. C. (1986) *J. Biol. Chem.* 261, 13744–13753.
17. Gross, E. & Morell, J. (1971) *J. Amer. Chem. Soc.* 93, 4634–4635.
18. Ho, S. N. et al (1989) *Appl. Environ. Microbiol.* 77, 51–59.
19. Holo, H. & Nes, I. F. (1989) *Appl. Environ. Microbiol.* 55, 3119–3123.
20. Horinouchi, S. & Weisblum, B. (1982) *J. Bacteriol.* 150, 804–814.
21. Horinouchi, S. & Weisbium, B. (1982) *J. Bacteriol.* 150, 815–825.
22. Horn, N. et al (1991) *Molec. Gen. Genet.* 228, 129–135.
23. Hugenholtz, J. & De Veer, J. C. M. (1991) In "*Nisin and novel lantibiotics*" (eds. G. Jung & H-S. Sahl) pp. 440–447. ESCOM, Leiden.
24. Humphreys, G. O. et al (1979) In "*Transformation—1978.*" (eds. Glover, S. W. & Butler, L. O.) pp. 254–279. Cotswold Press, Oxford.
25. Hurst, A. (1981) *Appl. Microbiol.* 27, 85–123.
26. Jung, G. (1990) In "*Nisin and novel lantibiotics*" (eds. G. Jung & H-S. Sahl) pp. 1–34. ESCOM, Leiden.
27. Kaletta, C. & Entian, K-D. (1989) *J. Bacteriol.* 171, 1597–1601.
28. Klein, C. et al (1992) *Appl. Env. Microbiol.* 58, 132–142.
29. Kuipers, O. P. et al (1991) In "*Nisin and novel lantibiotics*" (eds. G. Jung & H-S. Sahl) pp. 250–259. ESCOM, Leiden.
30. Lennox, E. S. (1955) *Virology* 1, 190–206.
31. Leenhouts, K. J. et al (1989) *Appl. Environ. Microbiol.* 55, 394–400.
32. Leenhouts, K. J. et al (1990) *Appl. Environ. Microbiol.* 56, 2726–2735.
33. Lewington, J. et al (1987) *Letts. Appl. Microbiol.* 5, 51–53.
34. Lian, L. Y. et al (1992) *J. Biochem.* (in press).
35. Maniatis, T. et al (1982) *Molecular cloning: a laboratory manual.* Cold Spring Harbor Laboratory, Cold Spring Harbor, N.Y.
36. McKay L. L. et al (1972) *Appl. Environ. Microbiol.* 23, 1090–1096.
37. Mulders, J. W. M. et al (1991) *Eur. J. Biochem.* 201, 581–584.
38. Rauch, P. J. G. et al (1991) In "*Nisin and novel lantibiotics*" (eds. G. Jung & H-S. Sahl) pp. 243–249. ESCOM, Leiden.
39. Rouch, D. A. et al (1987) *J. Gen. Micro.* 133, 3039–3052.
40. Sanger, F. et al (1980) *J. Mol. Biol.* 143, 161–178.
41. Schnell, N. et al (1992) *Eur. J. Biochem.* (in press).
42. Steen, M. T. et al (1991) *Appl. Environ. Microbiol.* 57, 1181–1188.
43. Terzaghi, B. E. & Sandine, W. E. (1975) *Appl. Microbiol.* 29, 807–813.
44. Tramer, J. & Fowler, G. G. (1964) *J. Sci. Food and Agri.* 15, 522–528.
45. Van De Ven, F. J. M. et al (1992) *Eur. J. Biochem.* (in press).
46. Van Rooijen, R. J. et al (1991) *J. Biol. Chem.* 266, 7176–7181.
47. Vieira, J. & Messing, J. (1982) *Gene* 19, 259–268.
48. Wakamiya, T. et al (1990) In "*Peptides—Chemistry, Structure and Biology*" (eds. J. E. River & G. R. Marshall) pp. 60–64. ESCOM, Leiden.
49. Zafarullah, M. et al (1981) *J. Bacteriol.* 146, 415–417.

We claim:

1. An organism which does not secrete a natural nisA nisin, but which expresses genes for nisin modification, immunity, and translocation out of the cell, wherein the organism is a lactococcal strain.

2. The organism according to claim 1 transformed with a coding sequence for a variant prenisin and, if necessary, appropriate regulatory sequences for expression thereof such that the organism secretes the variant nisin corresponding to the variant prenisin.

3. A method of producing the organism of claim 1 comprising selecting a nisin producing organism which contains a coding sequence for its natural nisA gene product and selectively deleting the coding sequence for its natural nisA gene product.

4. A method of producing the organism of claim 1 comprising selecting a nisin producing organism which contains a nisA gene and insertionally inactivating the nisA gene and restoring the activity of the genes for nisin modification, immunity, and translocation out of the cell.

5. The method according to claim 4 wherein the restoration of the activity of the genes for nisin modification, immunity, and translocation out of the cell is achieved by selection in media containing nisin.

6. A method according to any one of claims 3, 4 and 5 further comprising transforming the organism with a coding sequence for a variant prenisin and, if necessary, appropriate regulatory sequences for expression thereof, such that the organism secretes the variant nisin corresponding to the variant prenisin.

7. A process for producing a nisin comprising fermenting the organism of claim 2 and obtaining the nisin produced thereby.

8. The process according to claim 7 wherein the lactococcal strain is *Lactococcus lactis*.

9. The process according to claim 7 wherein the coding sequence for said variant prenisin comprises a codon other than a serine codon corresponding to a codon for a serine residue in unmodified prenisin which is converted to dehydroalanine in a first ring of mature nisin.

10. The process according to claim 8 wherein the coding sequence for said variant prenisin comprises a codon other than a serine codon corresponding to a codon for a serine residue in unmodified prenisin which is converted to dehydroalanine in a first ring of mature nisin.

11. The process according to claim 9 wherein said codon other than a serine codon is an alanine codon.

12. The process according to claim 10 wherein said codon other than a serine codon is an alanine codon.

13. An organism which is a *Lactococcus lactis* which does not secrete its natural nisA nisin, but which expresses genes for nisin modification, immunity, and translocation out of the cell.

14. The organism according to claim 13 transformed with a coding sequence for a variant prenisin and, if necessary, appropriate regulatory sequences for expression thereof such that the organism secretes the variant nisin corresponding to the variant prenisin.

15. A method of producing the organism of claim 13 comprising selecting a nisin producing organism which contains a coding sequence for its natural nisA gene product and selectively deleting the coding sequence for its natural nisA gene product.

16. A method of producing the organism of claim 13 comprising selecting a nisin producing organism which contains a nisA gene and insertionally inactivating the nisA gene and restoring the activity of the genes for nisin modification, immunity and translocation out of the cell.

17. The method according to claim 16 wherein the restoration of the activity of the genes for nisin modification, immunity and translocation out of the cell is achieved by selection in media containing nisin.

18. The method according to any one of claims 15, 16 and 17 further comprising transforming the organism with a coding sequence for a variant prenisin and, if necessary, appropriate regulatory sequences for expression thereof, such that the organism secretes the variant nisin corresponding to the variant prenisin.

\* \* \* \* \*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 448 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: join(88..258, 369..446)

(xi) SEQUENCE DESCRIPTION: SEQ ID NO:1:

```
AACGGNTCNG ATTAAATTCT GAAGTTTGTT AGATACAATG ATTTCGTTCG AAGGAACTAC        60

AAAATAAATT ATAAGGAGGC ACTCAAA ATG AGT ACA AAA GAT TTT AAC TTG           111
                             Met Ser Thr Lys Asp Phe Asn Leu
                              1               5

GAT TTG GTA TCT GTT TCG AAG AAA GAT TCA GGT GCA TCA CCA CGC ATT         159
Asp Leu Val Ser Val Ser Lys Lys Asp Ser Gly Ala Ser Pro Arg Ile
        10              15                  20

ACA AGT ATT NNN CTA TGT ACA CCC GGT TGT AAA ACA GGA GCT CTG ATG         207
Thr Ser Ile Xaa Leu Cys Thr Pro Gly Cys Lys Thr Gly Ala Leu Met
 25              30                  35                      40

GGT TGT AAC ATG AAA ACA GCA ACT TGT CAN TGT AGT ATT CAC GTA AGC         255
Gly Cys Asn Met Lys Thr Ala Thr Cys Xaa Cys Ser Ile His Val Ser
                 45                  50                  55

AAA TAACCAAATC AAAGGATAGT ATTTTGTTAG TTCAGACATG GATACTATCC              308
Lys

TATTTTTATA AGTTATTTAG GGTTGCTAAA TAGCTTATAA AAATAAAGAG AGGAAAAAAC       368

ATG ATA AAA AGT TCA TTT AAA GCT CAA CCG TTT TTA GTA AGA AAT ACA         416
Met Ile Lys Ser Ser Phe Lys Ala Gln Pro Phe Leu Val Arg Asn Thr
             60              65                  70

ATT TTA TCT CCA AAC GAT AAA CGG ANT TNT AC                              448
Ile Leu Ser Pro Asn Asp Lys Arg Xaa Xaa
     75              80

(2) INFORMATION FOR SEQ ID NO:2:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Thr Lys Asp Phe Asn Leu Asp Leu Val Ser Val Ser Lys Lys
 1               5                  10                  15

Asp Ser Gly Ala Ser Pro Arg Ile Thr Ser Ile Xaa Leu Cys Thr Pro
             20                  25                  30

Gly Cys Lys Thr Gly Ala Leu Met Gly Cys Asn Met Lys Thr Ala Thr
         35                  40                  45

Cys Xaa Cys Ser Ile His Val Ser Lys Met Ile Lys Ser Ser Phe Lys
     50                  55                  60

Ala Gln Pro Phe Leu Val Arg Asn Thr Ile Leu Ser Pro Asn Asp Lys
 65                  70                  75                  80

Arg Xaa Xaa (2) INFORMATION FOR SEQ ID NO:3:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GAAGACTTTC TTTCATAAAG TAATTTTTTT CCAAAGATAA TTCTCTTTTA ATTGTATCAT        60

AAAAGATAAT ATTTTCAAGG TAAAACAAAC AATTTCAAAC AAAAACAAAC GTTAGATGAT       120

GAAATAAGAA CAGAGGATTG ACGTATATTA GCTTAGGTCA GATTTTGTAT AAGACGAAAA       180
```

```
TAAAGTAGGA CCTCTTAATC AGTAAGTTAT AGAAAGTAAA AGACTTTTGT AATACCTGAA      240

TAGATATTTC ACGTCCATTT TGTGATGGAT TAAATGAACA AAAATGAACA ATAATTTAAC      300

GGTGTTATCT ATTTTTTAAA AAAACAAATA AAAAAAAACA AAAAATTAAC AAAAATAGTT      360

GCGTTTTGTT TGAATGTTTG ATATCATATA AACAAAGAAA TGATGAAAAC GTTATCTTGA      420

ACATTTTGCA AAATATTTTC TACTTCTACG TAGCATTTCG GATCCGATTA AATTCTGAAG      480

TTTGTTAGAT ACAATGATTT CGTTCGAAGG AACTACAAAA TAAATTATAA GGAGGCACTC      540

AAAATG                                                                546

(2) INFORMATION FOR SEQ ID NO:4:

(i) SEQUENCE CHARACTERISTICS:
        (A) LENGTH: 1313 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 90..1262

(xi) SEQUENCE DESCRIPTION: SEQ ID NO:4:
```

```
GGTAGTGTAA AATAAGTTGT GTAAACACAA AAAGGAATAA ATCCGTTATA GTAGAGTTGC       60

GAAACATTAC TAGAAAGAGA TTTATTCCT ATG ACT CAG TTT ACC ACA GAA CTA       113
                                 Met Thr Gln Phe Thr Thr Glu Leu
                                   1               5

CTT AAC TTC CTA GCC CAA AAG CAA GAT ATT GAT GAA TTT TTC CGT ACT       161
Leu Asn Phe Leu Ala Gln Lys Gln Asp Ile Asp Glu Phe Phe Arg Thr
 10                  15                  20

TCT CTT GAA ACT GCT ATG AAT GAT CTG CTT CAA GCA GAG TTA TCA GCC       209
Ser Leu Glu Thr Ala Met Asn Asp Leu Leu Gln Ala Glu Leu Ser Ala
 25                  30                  35                  40

TTT TTA GGG TAT GAA CCT TAC GAT AAA GTA GGC TAT AAT TCT GGG AAT       257
Phe Leu Gly Tyr Glu Pro Tyr Asp Lys Val Gly Tyr Asn Ser Gly Asn
                 45                  50                  55

AGT CGT AAC GGA AGC TAT TCA CGG CAA TTT GAA ACC AAA TAT GGG ACT       305
Ser Arg Asn Gly Ser Tyr Ser Arg Gln Phe Glu Thr Lys Tyr Gly Thr
             60                  65                  70

GTT CAG TTG AGC ATT CCT AGA GAT CGT AAT GGG AAC TTT AGT CCA GCT       353
Val Gln Leu Ser Ile Pro Arg Asp Arg Asn Gly Asn Phe Ser Pro Ala
         75                  80                  85

TTG CTT CCC GCT TAT GGA CGT CGA GAT GAC CAC TTG GAA GAG ATG GTT       401
Leu Leu Pro Ala Tyr Gly Arg Arg Asp Asp His Leu Glu Glu Met Val
     90                  95                 100

ATC AAA CTC TAT CAA ACC GGT GTA ACG ACT CGA GAA ATT AGT GAT ATC       449
Ile Lys Leu Tyr Gln Thr Gly Val Thr Thr Arg Glu Ile Ser Asp Ile
105                 110                 115                 120

ATC GAG CGA ATG TAT GGT CAT CAC TAT AGT CCT GCC ACA ATT TCT AAT       497
Ile Glu Arg Met Tyr Gly His His Tyr Ser Pro Ala Thr Ile Ser Asn
                125                 130                 135

ATC TCA AAA GCA ACT CAG GAG AAT GTC GCT ACT TTT CAT GAG CGA AGC       545
Ile Ser Lys Ala Thr Gln Glu Asn Val Ala Thr Phe His Glu Arg Ser
            140                 145                 150

TTA GAA GCC AAT TAC TCT GTT TTA TTT CTT GAC GGA ACC TAT CTT CCA       593
Leu Glu Ala Asn Tyr Ser Val Leu Phe Leu Asp Gly Thr Tyr Leu Pro
        155                 160                 165

TTA AGA CGT GGA ACC GTT AGT AAA GAA TGT ATT CAT ATC GCA CTT GGC       641
Leu Arg Arg Gly Thr Val Ser Lys Glu Cys Ile His Ile Ala Leu Gly
```

```
                170                 175                 180
ATT ACA CCA GAA GGA CAG AAG GCT GTT CTT GGA TAT GAA ATC GCC CCA      689
Ile Thr Pro Glu Gly Gln Lys Ala Val Leu Gly Tyr Glu Ile Ala Pro
185                 190                 195                 200

AAT CAA AAT AAT GCT TCT TGG TCC ACC CTG TTA GAC AAG CTT CAA AAC      737
Asn Gln Asn Asn Ala Ser Trp Ser Thr Leu Leu Asp Lys Leu Gln Asn
                205                 210                 215

CAA GGA ATC CAA CAG GTT TCT CTT GTA GTG ACC GAT GGC TTC AAG GGG      785
Gln Gly Ile Gln Gln Val Ser Leu Val Val Thr Asp Gly Phe Lys Gly
                220                 225                 230

CTT GAA CAG ATT ATC AGT CAG GCT TAC CCA TTA GCT AAA CAA CAA CGT      833
Leu Glu Gln Ile Ile Ser Gln Ala Tyr Pro Leu Ala Lys Gln Gln Arg
                235                 240                 245

TGC TTA ATT CAT ATT AGT CGA AAT CTA GCT AGT AAA GTG AAA CGA GCA      881
Cys Leu Ile His Ile Ser Arg Asn Leu Ala Ser Lys Val Lys Arg Ala
                250                 255                 260

GAT AGA GCG GTT ATT CTG GAG CAA TTT AAA ACG ATT TAT CGT GCT GAA      929
Asp Arg Ala Val Ile Leu Glu Gln Phe Lys Thr Ile Tyr Arg Ala Glu
265                 270                 275                 280

AAT TTA GAA ATG GCA GTG CAA GCT TTA GAG AAC TTT ATC GCC GAA TGG      977
Asn Leu Glu Met Ala Val Gln Ala Leu Glu Asn Phe Ile Ala Glu Trp
                285                 290                 295

AAA CCA AAG TAT AGG AAA GTC ATG GAA AGT CTG GAG AAT ACG GAT AAT     1025
Lys Pro Lys Tyr Arg Lys Val Met Glu Ser Leu Glu Asn Thr Asp Asn
                300                 305                 310

CTT TTA ACT TTT TAT CAG TTT CCC TAC CAG ATT TGG CAC AGC ATT TAT     1073
Leu Leu Thr Phe Tyr Gln Phe Pro Tyr Gln Ile Trp His Ser Ile Tyr
                315                 320                 325

TCG ACA AAC CTC ATT GAG TCT CTT AAC AAA GAA ATC AAA CGT CAA ACG     1121
Ser Thr Asn Leu Ile Glu Ser Leu Asn Lys Glu Ile Lys Arg Gln Thr
330                 335                 340

AAA AAG AAG GTT CTT TTT CCT AAC GAG GAG GCT CTG GAA CGT TAC TTA     1169
Lys Lys Lys Val Leu Phe Pro Asn Glu Glu Ala Leu Glu Arg Tyr Leu
345                 350                 355                 360

GTT ACT TTG TTT GAA GAT TAT AAT TTC AAG CAA AGT CAA CGC ATC CAT     1217
Val Thr Leu Phe Glu Asp Tyr Asn Phe Lys Gln Ser Gln Arg Ile His
                365                 370                 375

AAA GGG TTT GGC CAA TGT GCT GAC ACA CTT GAA AGC TTA TTT GAT         1262
Lys Gly Phe Gly Gln Cys Ala Asp Thr Leu Glu Ser Leu Phe Asp
                380                 385                 390

TAATATTCTT CAACTCTACT TGAGTGTTTA CACATAATTA TTGACAGTAT C            1313

(2) INFORMATION FOR SEQ ID NO:5:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:5:

Met Thr Gln Phe Thr Thr Glu Leu Leu Asn Phe Leu Ala Gln Lys Gln
1               5                   10                  15

Asp Ile Asp Glu Phe Phe Arg Ser Leu Glu Thr Ala Met Asn Asp
                20                  25                  30

Leu Leu Gln Ala Glu Leu Ser Ala Phe Leu Gly Tyr Glu Pro Tyr Asp
                35                  40                  45

Lys Val Gly Tyr Asn Ser Gly Asn Ser Arg Asn Gly Ser Tyr Ser Arg
50                  55                  60
```

Gln Phe Glu Thr Lys Tyr Gly Thr Val Gln Leu Ser Ile Pro Arg Asp
 65                  70                  75                  80

Arg Asn Gly Asn Phe Ser Pro Ala Leu Leu Pro Ala Tyr Gly Arg Arg
             85                  90                  95

Asp Asp His Leu Glu Glu Met Val Ile Lys Leu Tyr Gln Thr Gly Val
            100                 105                 110

Thr Thr Arg Glu Ile Ser Asp Ile Ile Glu Arg Met Tyr Gly His His
            115                 120                 125

Tyr Ser Pro Ala Thr Ile Ser Asn Ile Ser Lys Ala Thr Gln Glu Asn
130                 135                 140

Val Ala Thr Phe His Glu Arg Ser Leu Glu Ala Asn Tyr Ser Val Leu
145                 150                 155                 160

Phe Leu Asp Gly Thr Tyr Leu Pro Leu Arg Arg Gly Thr Val Ser Lys
            165                 170                 175

Glu Cys Ile His Ile Ala Leu Gly Ile Thr Pro Glu Gly Gln Lys Ala
            180                 185                 190

Val Leu Gly Tyr Glu Ile Ala Pro Asn Gln Asn Asn Ala Ser Trp Ser
            195                 200                 205

Thr Leu Leu Asp Lys Leu Gln Asn Gln Gly Ile Gln Gln Val Ser Leu
            210                 215                 220

Val Val Thr Asp Gly Phe Lys Gly Leu Glu Gln Ile Ile Ser Gln Ala
225                 230                 235                 240

Tyr Pro Leu Ala Lys Gln Gln Arg Cys Leu Ile His Ile Ser Arg Asn
            245                 250                 255

Leu Ala Ser Lys Val Lys Arg Ala Asp Arg Ala Val Ile Leu Glu Gln
            260                 265                 270

Phe Lys Thr Ile Tyr Arg Ala Glu Asn Leu Glu Met Ala Val Gln Ala
            275                 280                 285

Leu Glu Asn Phe Ile Ala Glu Trp Lys Pro Lys Tyr Arg Lys Val Met
            290                 295                 300

Glu Ser Leu Glu Asn Thr Asp Asn Leu Leu Thr Phe Tyr Gln Phe Pro
305                 310                 315                 320

Tyr Gln Ile Trp His Ser Ile Tyr Ser Thr Asn Leu Ile Glu Ser Leu
            325                 330                 335

Asn Lys Glu Ile Lys Arg Gln Thr Lys Lys Val Leu Phe Pro Asn
            340                 345                 350

Glu Glu Ala Leu Glu Arg Tyr Leu Val Thr Leu Phe Glu Asp Tyr Asn
            355                 360                 365

Phe Lys Gln Ser Gln Arg Ile His Lys Gly Phe Gly Gln Cys Ala Asp
            370                 375                 380

Thr Leu Glu Ser Leu Phe Asp
385                 390

(2) INFORMATION FOR SEQ ID NO:6:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "promoter"

(xi) SEQUENCE DESCRIPTION: SEQ ID NO:6:

ACGTGCTATC ACTTGAAGCT TATTGATTAA TATTCTTCAA CTCTACTTGA GTGTTTACAC    60

ATAATTATTG ACAGTATCCA ATTCTTATCT CTTTTCAATA          100

(2) INFORMATION FOR SEQ ID NO:7:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "promoter"

(xi) SEQUENCE DESCRIPTION: SEQ ID NO:7:

ACGTGCTATC ACTTGAAGCT TATTGATTAA TATTCTTCAA CTCTACTGCA ACTTGTCATT          60

GTAGCATTCA CGTAAGCAAA TAACCAAATC AAAGGATAGT          100

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

AAGAATCTCT CATGAGT          17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

CCATGTCTGA ACTAACA          17

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

GTGGAATACG GGTTTG          16

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "primer"

(xi) SEQUENCE DESCRIPTION: SEQ ID NO:11:

TAAATAATTT ATAGCTATTG                                                  20

(2) INFORMATION FOR SEQ ID NO:12:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:12:

CAGAGCTCTG ATGGGTTG                                                    18

(2) INFORMATION FOR SEQ ID NO:13:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:13:

GTAGAATTCC GTTTATCGTT TGGAG                                            25

(2) INFORMATION FOR SEQ ID NO:14:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:14:

GCAACTTGTC AGTGTAGTAT TCAC                                             24

(2) INFORMATION FOR SEQ ID NO:15:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:15:

GTGAATACTA CACTGACAAG TTGC                                             24

(2) INFORMATION FOR SEQ ID NO:16:

(i) SEQUENCE CHARACTERISTICS:
              (A) LENGTH: 28 base pairs
              (B) TYPE: nucleic acid
              (C) STRANDEDNESS: single
              (D) TOPOLOGY: linear

```
         (ii) MOLECULE TYPE: other nucleic acid
              (A) DESCRIPTION: /desc = "primer"

(xi) SEQUENCE DESCRIPTION: SEQ ID NO:16:

AACGGATCCG ATTAAATTCT GAAGTTTG                                           28

(2) INFORMATION FOR SEQ ID NO:17:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:17:

TCAGAGCTCC TGTTTTACAA                                                    20

(2) INFORMATION FOR SEQ ID NO:18:

(i) SEQUENCE CHARACTERISTICS:
              (A) LENGTH: 40 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "primer"

(xi) SEQUENCE DESCRIPTION: SEQ ID NO:18:

TCAGAGCTCC TGTTTTACAA CCGGGTGTAC ATAGTGCAAT                               40

(2) INFORMATION FOR SEQ ID NO:19:

(i) SEQUENCE CHARACTERISTICS:
              (A) LENGTH: 34 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 2
              (D) OTHER INFORMATION: /product= "Dhb"

(ix) FEATURE:
              (A) NAME/KEY: Modified-site
              (B) LOCATION: 5
              (D) OTHER INFORMATION: /product= "Dha or Ala"

(ix) FEATURE:
              (A) NAME/KEY: Modified-site
              (B) LOCATION: 8
              (D) OTHER INFORMATION: /product= "Abu"

(ix) FEATURE:
              (A) NAME/KEY: Modified-site
              (B) LOCATION: 13
              (D) OTHER INFORMATION: /product= "Abu"

(ix) FEATURE:
              (A) NAME/KEY: Modified-site
              (B) LOCATION: 23
              (D) OTHER INFORMATION: /product= "Abu"

(ix) FEATURE:
              (A) NAME/KEY: Modified-site
              (B) LOCATION: 25
              (D) OTHER INFORMATION: /product= "Abu"
```

```
    (ix) FEATURE:
         (A) NAME/KEY: Modified-site
         (B) LOCATION: 27
         (D) OTHER INFORMATION: /product= "His or Gln"

(ix) FEATURE:
         (A) NAME/KEY: Modified-site
         (B) LOCATION: 33
         (D) OTHER INFORMATION: /product= "Dha"

(xi) SEQUENCE DESCRIPTION: SEQ ID NO:19:

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Xaa Ala Ser Ile His Val
            20                  25                  30

Xaa Lys (2) INFORMATION FOR SEQ ID NO:20:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "promoter"

(xi) SEQUENCE DESCRIPTION: SEQ ID NO:20:

TATTGAAAAG AGATAAGAAT TGGATACTGT CAATAATTAT GTGTAAACAC TCAAGTAGAG        60

TTGAAGAATA TTAATCAATA AGCTTCAAGT GATAGCACGT                             100

(2) INFORMATION FOR SEQ ID NO:21:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "promoter"

(xi) SEQUENCE DESCRIPTION: SEQ ID NO:21:

ACTATCCTTT GATTTGGTTA TTTCGTTACG TGAATGCTAC AATGACAAGT TGCAGTAGAG        60

TTGAAGAATA TTAATCAATA AGCTTCAAGT GATAGCACGT                             100
```